(12) United States Patent
Bartz

(10) Patent No.: US 10,603,200 B2
(45) Date of Patent: *Mar. 31, 2020

(54) SYSTEM AND APPARATUS FOR ADJUSTABLE GASTRIC BYPASS

(71) Applicant: LSI Solutions, Inc., Victor, NY (US)

(72) Inventor: Robert E. Bartz, Lancaster, NY (US)

(73) Assignee: LSI Solutions, Inc., Victor, NY (US)

(*) Notice: Subject to any disclaimer, the term of this patent is extended or adjusted under 35 U.S.C. 154(b) by 290 days.

This patent is subject to a terminal disclaimer.

(21) Appl. No.: 15/436,339

(22) Filed: Feb. 17, 2017

(65) Prior Publication Data

US 2017/0224513 A1    Aug. 10, 2017

Related U.S. Application Data

(63) Continuation of application No. 14/457,210, filed on Aug. 12, 2014, now Pat. No. 9,603,694.

(51) Int. Cl.
*A61F 5/00* (2006.01)
*A61F 2/04* (2013.01)

(52) U.S. Cl.
CPC .............. *A61F 5/0076* (2013.01); *A61F 2/04* (2013.01); *A61F 5/0043* (2013.01); *A61F 2002/044* (2013.01); *A61F 2002/045* (2013.01)

(58) Field of Classification Search
CPC ........ A61F 2/04; A61F 5/0076; A61F 5/0079; A61F 2002/045
See application file for complete search history.

(56) References Cited

U.S. PATENT DOCUMENTS

2005/0240279 A1* 10/2005 Kagan .................. A61F 2/04
                                                    623/23.65
2013/0190892 A1*  7/2013 Schwab ................ A61F 5/003
                                                    623/23.68

* cited by examiner

*Primary Examiner* — Leslie R Deak
(74) *Attorney, Agent, or Firm* — David J. Gervasi; Christopher B. Miller

(57) ABSTRACT

An apparatus for gastric bypass is disclosed. The apparatus for gastric bypass includes a primary passage having an input and an output. The apparatus also includes a bypass conduit, coupled to the primary passage, having an input and an output, wherein the passage input is interspersed with the conduit input. The apparatus further has a primary regulator coupled to the primary passage and adjustable to control a primary flow profile from the input to the output of the primary passage. The apparatus also has a bypass regulator coupled to the bypass conduit and adjustable to control a bypass flow profile from the input to the output of the bypass conduit.

32 Claims, 18 Drawing Sheets

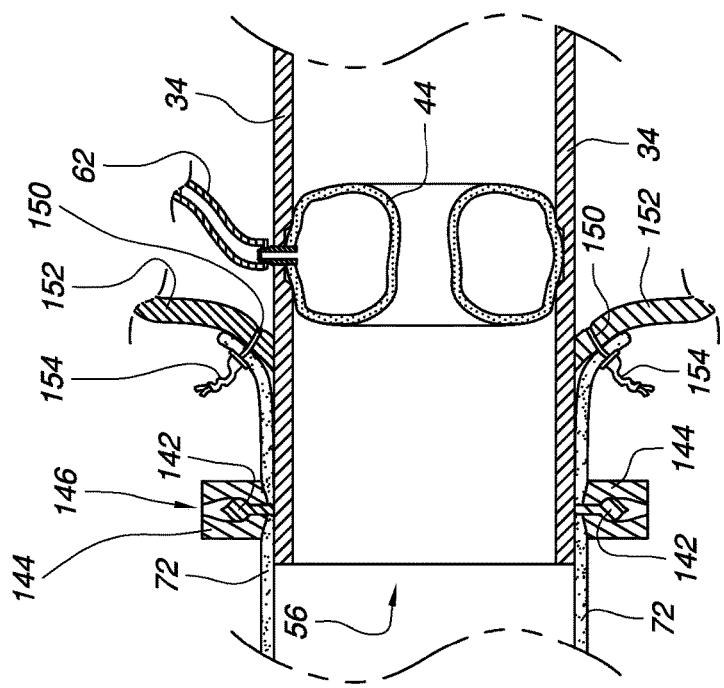
FIG. 13
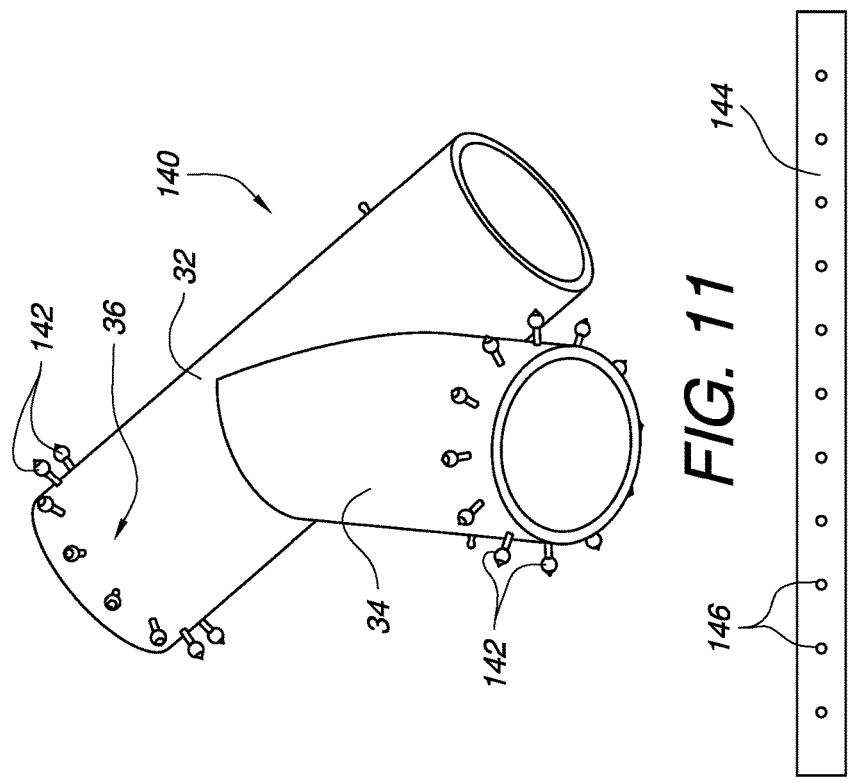
FIG. 11
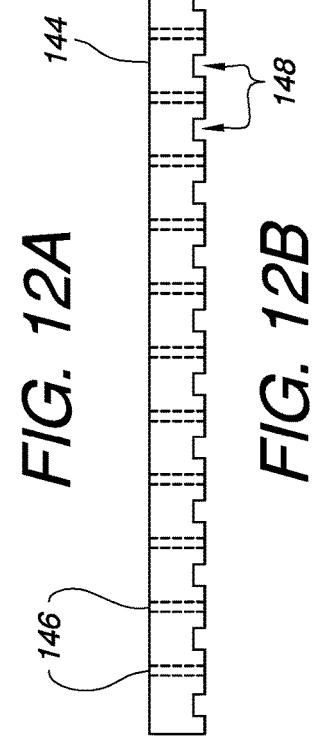
FIG. 12A
FIG. 12B

SYSTEM AND APPARATUS FOR ADJUSTABLE GASTRIC BYPASS

RELATED APPLICATIONS

This application is a continuation of U.S. patent application Ser. No. 14/457,210 filed Aug. 12, 2014 and entitled "SYSTEM AND APPARATUS FOR ADJUSTABLE GASTRIC BYPASS", which is issued as U.S. Pat. No. 9,603,694 after the filing of this application. The Ser. No. 14/457,210 application is hereby incorporated by reference in its entirety.

FIELD

The claimed invention relates to gastric bypass, and more specifically to a system and apparatus which enable an adjustable gastric bypass.

BACKGROUND

The Centers for Disease Control and Prevention (CDC) estimate that 110,000 Americans die as a result of obesity each year, and that one-third of all cancers are directly related to excess weight. Obesity is also a leading contributor to many health problems, including the development of Type-II diabetes. The CDC reports that nearly thirty-five percent of adults in the United States are obese. Obesity is a growing problem around the world, and physicians are bringing needed attention to the issue and associated risks.

In addition to raising awareness on obesity issues, healthcare providers also encourage people to lose excess weight by improving the nutritional content of their diets, eating less, and increasing their amount of exercise. Unfortunately, however, for a variety of reasons, these more conservative weight-loss approaches are not successful for some people. In such cases, where significant weight loss is needed, but is not being achieved, some people have taken advantage of surgical procedures to limit the amount of food their stomach can hold, thereby forcing them to eat less and lose excess weight.

In the United States, there are roughly 200,000 weight-loss surgeries each year, which the American Society for Metabolic & Bariatric Surgery reports is only one percent of the eligible population for such surgeries. Surgical candidates have a choice between a variety of surgical procedures, however, the procedures can be grouped into two main categories: gastric bypass surgery and laparoscopic band surgery. In gastric bypass surgery, a patient's stomach is stitched, stapled, or divided to drastically reduce the size of the stomach. A portion of the patient's small intestine is then attached between the newly created small stomach pouch and a portion of the small intestine well after the stomach, thereby bypassing the stomach and a portion of the small intestine. Successful gastric bypass patients are unable to ingest large quantities of food and are also unable to absorb as many nutrients as they could before their surgical procedure. As a result gastric bypass patients report excellent weight loss results.

Unfortunately, gastric bypass surgery is not easily undone. In certain cases, patients do not adjust well to the gastric bypass surgery. The causes for adverse gastric bypass health reactions vary, but a major contributor can include decreased absorption of one or more key nutrients due to the effective shortening of the gastrointestinal tract and/or patient failure to adhere to a strictly modified diet that may have required increased concentrations of certain nutrients. Similar gastric bypass complications can arise if a patient becomes pregnant. In such a situation, even though the patient might be adjusting well to the reduced nutritional intake, the patient's body would likely not be able to keep up with the dramatically increased nutritional needs of a growing unborn baby. In any of these situations, it is often impractical or impossible to surgically reverse the gastric bypass in order to increase the patient's nutritional intake as needed. Thus, decisions to have gastric bypass surgery are not taken lightly.

By comparison, laparoscopic band surgery has provided a less invasive, adjustable option for obese candidates. The procedure involves the placement of an adjustable band around a patient's stomach. The tightness of the stomach band can be adjusted during a visit to a doctor using a control port placed near the patient's skin surface. As the band is tightened, the patient's stomach fills up more quickly when eating, causing patients to eat less. Since the food still passes through an unmodified digestive tract, the full nutritional content of the ingested food can be absorbed. Furthermore, in cases with complications, the laparoscopic band can be loosened or even removed to allow for more nutritional intake.

Unfortunately, despite the many advantages of laparoscopic band surgery, gastric bypass surgery has been shown to produce dramatically more effective weight loss and health benefits within the first year following the surgical procedure when compared to laparoscopic band surgery. For example, a University of California-San Francisco study, comparing gastric bypass patients to laparoscopic band patients, found that the gastric bypass patients lost a higher percentage of excess weight (64% versus 36%) and had an increased resolution in Type-II diabetes (76% versus 50%) after one year. Despite some of the downsides to gastric bypass surgery, such dramatically better weight loss results and health improvements can be appealing to patients suffering from obesity and who are in need of fast improvements to their health.

Therefore, there is a need for improved gastric bypass methods, apparatuses, and systems that can provide adjustment and even reversal benefits which are currently lacking, while still enabling top weight-loss and health benefits.

SUMMARY

An apparatus for gastric bypass is disclosed. The apparatus for gastric bypass includes a primary passage having an input and an output. The apparatus also includes a bypass conduit, coupled to the primary passage, having an input and an output, wherein the passage input is interspersed with the conduit input. The apparatus further has a primary regulator coupled to the primary passage and adjustable to control a primary flow profile from the input to the output of the primary passage. The apparatus also has a bypass regulator coupled to the bypass conduit and adjustable to control a bypass flow profile from the input to the output of the bypass conduit.

A system for gastric bypass is also disclosed. The system for gastric bypass includes an apparatus for gastric bypass, a primary fluid access point, and a bypass fluid access point. The apparatus for gastric bypass includes a primary passage having an input and an output; a bypass conduit, coupled to the primary passage, having an input and an output, wherein the passage input is interspersed with the conduit input; a primary regulator coupled to the primary passage and adjustable to control a primary flow profile from the input to the output of the primary passage; and a bypass regulator coupled to the bypass conduit and adjustable to control a bypass flow profile from the input to the output of the bypass conduit.

Another apparatus for gastric bypass is disclosed. The apparatus includes a substantially straight primary passage having an input and an output. The input of the primary passage comprises an esophageal interface. The apparatus also includes a substantially straight bypass conduit having an input and an output. The bypass conduit is coupled to the primary passage such that: 1) a longitudinal axis of the primary passage forms an acute angle with a longitudinal axis of the bypass conduit as measured between the output of the primary passage and the output of the bypass conduit; and 2) food received from an esophagus must pass through at least a portion of the primary passage input in order to reach the bypass conduit input. The apparatus also includes a primary inflatable regulator coupled to the primary passage and adjustable to control a primary flow profile from the input to the output of the primary passage. The apparatus also includes a bypass inflatable regulator coupled to the bypass conduit and adjustable to control a bypass flow profile from the input to the output of the bypass conduit. The apparatus further includes a primary fluid connector located in alignment with and coupled to the primary inflatable regulator. The apparatus also includes a bypass fluid connector located in alignment with and coupled to the bypass inflatable regulator.

BRIEF DESCRIPTION OF THE DRAWINGS

FIGS. 4A-1 and 4A-2 illustrate cross-sectional views of one embodiment of an inflatable regulator for use in an apparatus for gastric bypass in both open and closed configurations, respectively.

FIGS. 4B-1 and 4B-2 illustrate cross-sectional views of another embodiment of an inflatable regulator for use in an apparatus for gastric bypass in both open and closed configurations, respectively.

FIG. 11 is a perspective view of another embodiment of an apparatus for gastric bypass having multiple piercing latches on an esophageal interface and on a bypass conduit to assist with installation of the apparatus.

FIGS. 12A and 12B illustrate top and side views, respectively, of one embodiment of an attachment band configured to help hold tissue against an outside surface of the apparatus for gastric bypass from FIG. 11.

FIG. 13 is a cross-sectional view of a portion of the bypass conduit from the apparatus of FIG. 11 showing one possible attachment embodiment for tissues outside the stomach and for sealing to tissues of the stomach.

Figure 1:
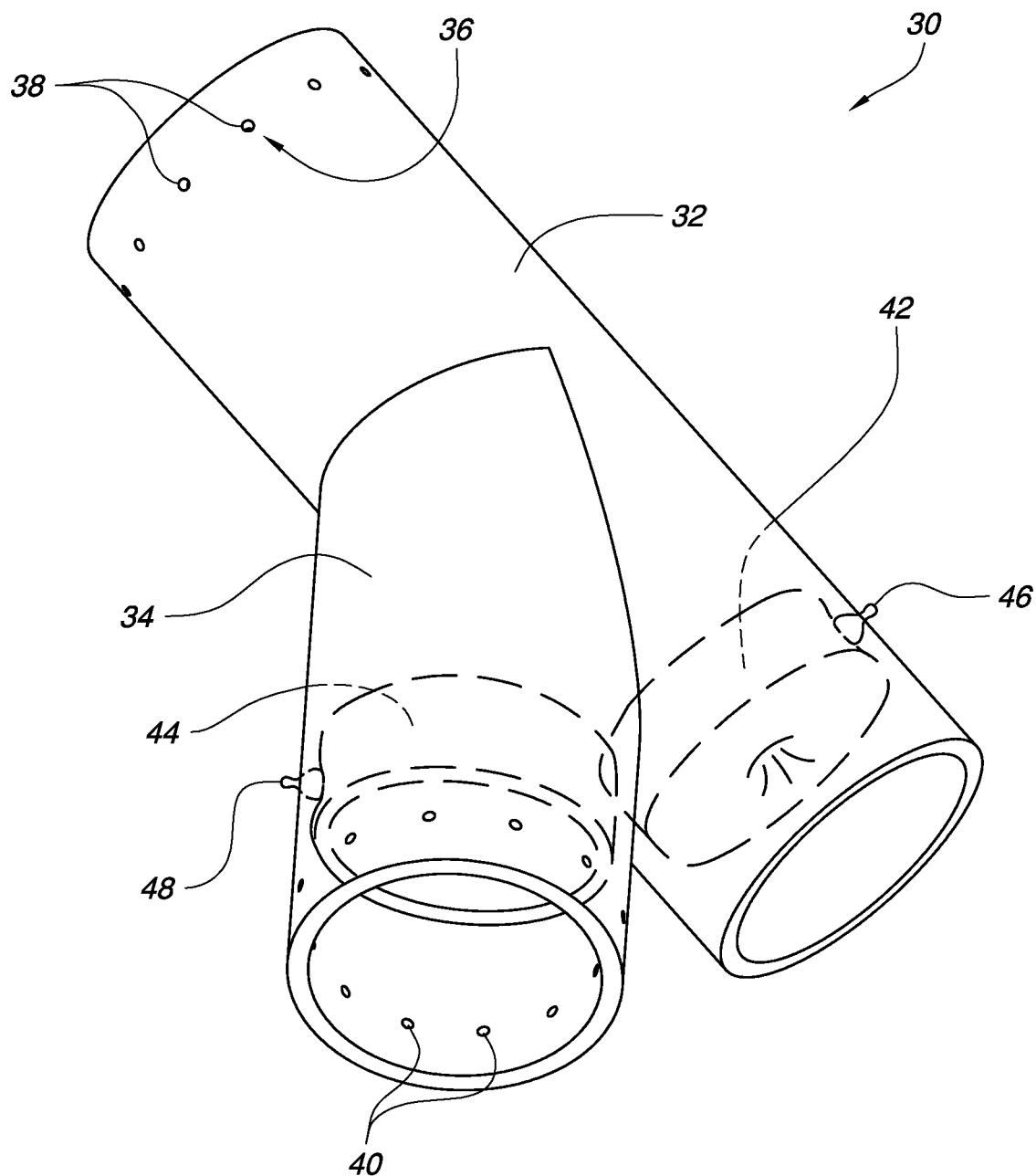
FIG. 1 is a perspective view of one embodiment of an apparatus for gastric bypass.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of one embodiment of an apparatus for gastric bypass 30. The gastric bypass apparatus 30 has a primary passage 32 and a bypass conduit 34. The primary passage 32 and the bypass conduit 34 may be formed of any rigid or flexible biocompatible material, including, but not limited to plastic, silicone, or even metal. In some embodiments, the material may not be able to be sutured. In such cases, suitable attachment points may be provided to an esophageal interface 36 of the apparatus 30. One non-limiting example of suitable attachment points may include suture holes 38. Depending on the embodiment, suture holes 40 may also be provided on the bypass conduit 34 to assist with connection of bypass tissue to the apparatus 30. The apparatus 30 also has a primary regulator 42 in the primary passage 32 and a bypass regulator 44 in the bypass conduit 34. In this embodiment, the primary regulator 42 is coupled to a primary fluid connector 46, while the bypass regulator 44 is coupled to a bypass fluid connector 48. The features and operation of the primary and bypass regulators 42, 44 and fluid connectors 46, 48 will be discussed in more detail below.

Figure 2:
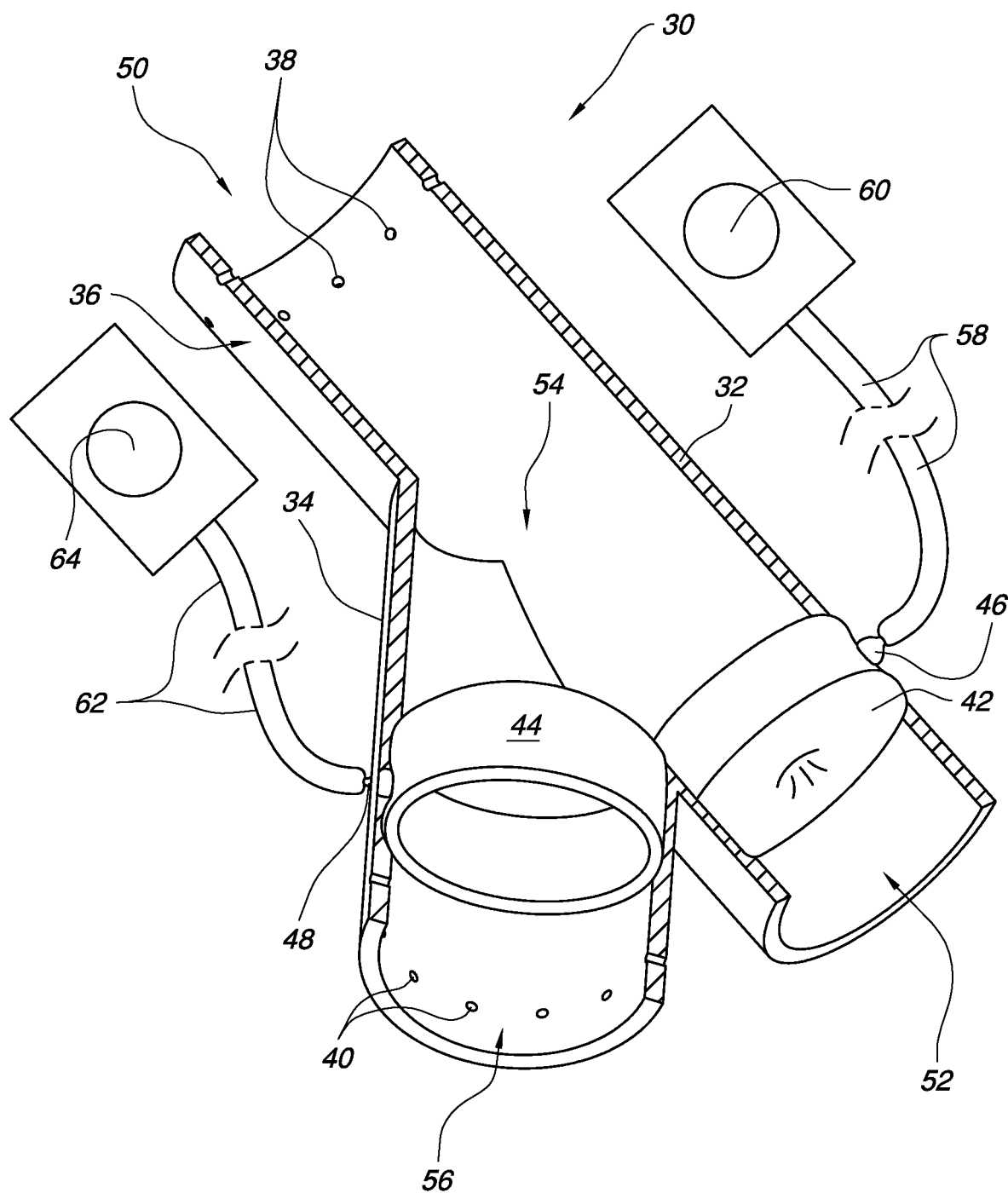
FIG. 2 is a partially cross-sectioned, perspective view of the embodied apparatus for gastric bypass from FIG. 1.

FIG. 2 is a partially cross-sectioned, perspective view of the embodied gastric bypass apparatus 30 of FIG. 1. The primary passage 32 has an input 50 and an output 52.

Likewise, the bypass conduit 34 has an input 54 and an output 56. The primary passage input 50 is interspersed with the bypass conduit input 54, meaning that the two inputs are at least partially in contact or communication with each other. In this embodiment, the primary passage input 50 must be passed through in order to reach the bypass conduit input 54. In other embodiments, the opposite could be the case: that the bypass conduit input must be passed through in order to reach the primary passage input. In still other embodiments, even though the primary passage input and the bypass conduit input are interspersed, there may still be at least a portion of both inputs which can be reached without passing through the other.

The primary regulator 42 is coupled to the primary passage 32 and is adjustable to control a primary flow profile from the input 50 to the output 52 of the primary passage 32. Likewise, the bypass regulator 44 is coupled to the bypass conduit 34 and is adjustable to control a bypass flow profile from the input 54 to the output 56 of the bypass conduit 34. The flow profiles can be considered to be a measure of how open or how closed each regulator 42, 44 is. Alternately, the flow profiles can represent an actual or estimated amount of material able to pass through each regulator 42, 44 depending on how open or how closed each regulator 42, 44 is.

In the embodiments illustrated herein, the primary regulator 42 and the bypass regulator 44 each are shown to be an inflatable device, such as, but not limited to a silicone balloon. In the embodiment of FIG. 2, the primary regulator 42 and the bypass regulator 44 are each shown as an inflatable balloon having a donut-like shape. Other embodiments may have one or more inflatable balloons having other shapes. For inflatable embodiments, the primary regulator 42 and the bypass regulator 44 may be filled with controllable amounts of fluid to set the inflation amount, and therefore the flow profile for each regulator 42, 44. The fluid can include any suitable liquid, gas, gel, etc. As one non-limiting example, a saline solution could be a suitable fluid for use with this apparatus.

The primary fluid connector 46 (coupled to the primary regulator 42) is configured to be coupled to one end of a primary fluid supply tube 58. The other end of the primary fluid supply tube 58 can be coupled to a primary fluid access point 60. Likewise, the bypass fluid connector 48 (coupled to the bypass regulator 44) is configured to be coupled to one end of a bypass fluid supply tube 62. The other end of the bypass fluid supply tube 62 can be coupled to a bypass fluid access point 64. The bypass fluid access points 60, 64 can either be located outside of a patient's body or, preferably, are implanted inside the patient's body just under the skin. Each bypass fluid access point 60, 64 can be made from a variety of materials, including, but not limited to metals, alloys, plastics, rubber, or a combination thereof. Each bypass fluid access point 60, 64 may have a fluid reservoir surrounded on at least one side by a self-sealing septum or similar device through which a needle may be inserted and withdrawn. A needle may be used with a syringe or similar device to add or remove fluid from the system. Fluid inserted into a fluid access point 60, 64 will pass through its respective fluid supply tube 58, 62, through its respective fluid connector 46, 48, and into its respective regulator 42, 44. The addition of fluid will tend to expand the regulator, thereby shrinking or eventually completely closing off an opening in the regulator. Conversely, fluid can be removed from the regulator 42, 44 by withdrawing fluid from a respective fluid access point 60, 64. The removal of fluid will tend to contract the regulator, thereby growing or eventually completely expanding the opening in the regulator. As illustrated in the embodiment of FIG. 2, the primary regulator 42 has been filled with enough fluid to completely close the regulator 42, thereby preventing any flow of material from the primary passage input 50 to the primary passage output 52. As also illustrated in the embodiment of FIG. 2, the bypass regulator 44 has been drained of enough fluid to completely open the regulator 44, thereby allowing full flow of material to pass from the bypass conduit input 54 to the bypass conduit output 56.

Figure 3:
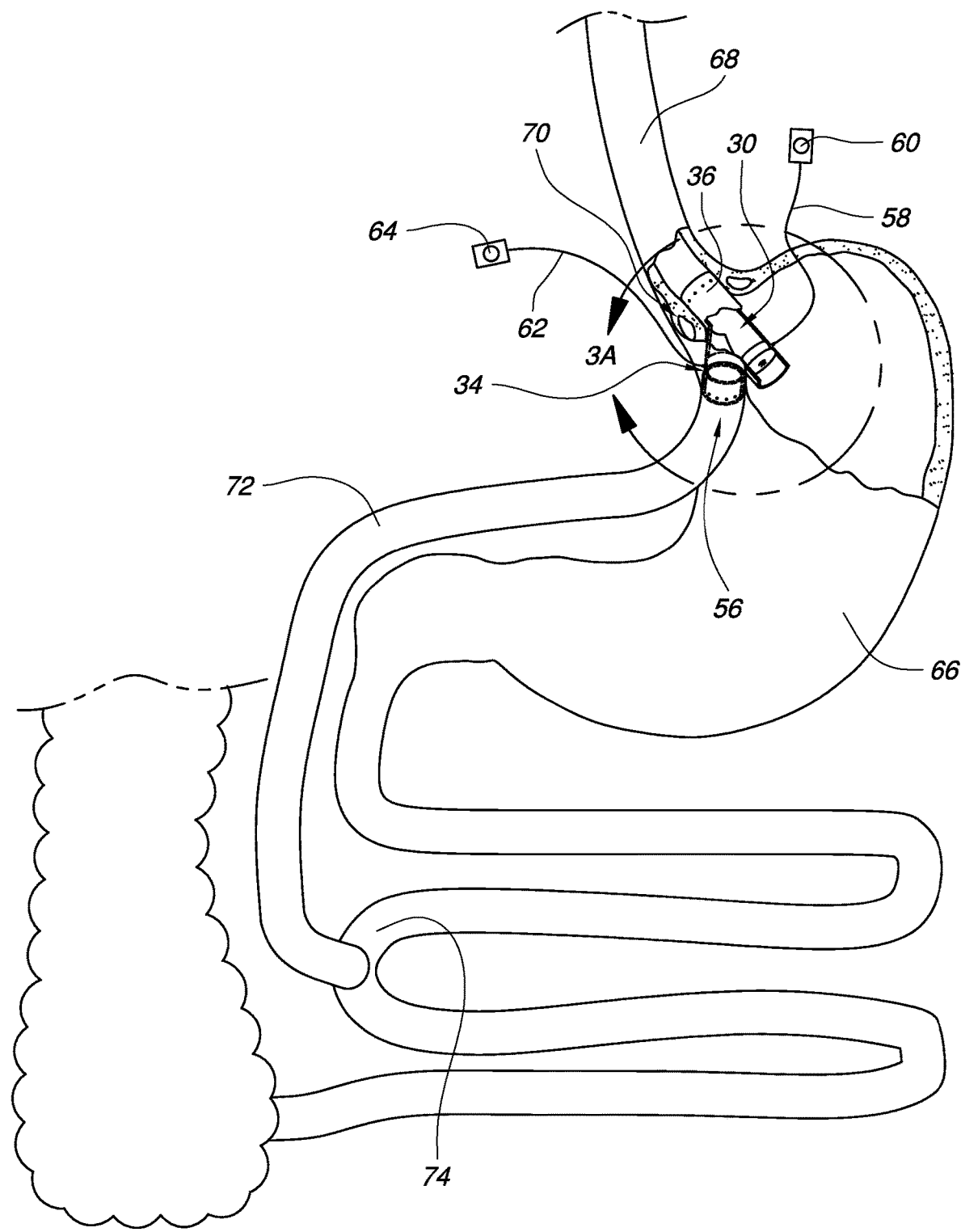
FIG. 3 is a partially cross-sectioned illustration of the apparatus for gastric bypass from FIG. 1 in one possible installed orientation for providing an adjustable gastric bypass to a patient.

FIG. 3 is a partially cross-sectioned illustration of the gastric bypass apparatus 30 from FIG. 1 in one possible installed orientation for providing an adjustable gastric bypass to a patient. Access to the stomach 66 can be gained by incision during a surgical procedure. Alternately or additionally, access the stomach 66 may be obtained through the mouth, throat, and esophagus 68. Embodiments of the gastric bypass apparatus 30 which are flexible may encourage introduction of the apparatus 30 into the stomach through the esophagus 68. In either case, the esophageal interface 36 of the apparatus 30 can be placed into the esophagus 68 near the esophageal sphincter 70. The apparatus 30 can be rotated so that the bypass conduit 34 faces a desired bypass direction within the stomach 66. In this example, the bypass conduit 34 is oriented slightly towards the patient's right side. Although not illustrated in this view, once a desired bypass orientation is obtained, the esophageal interface 36 may be sutured or otherwise attached to the esophagus 68 or nearby tissue. The bypass conduit output 56 is passed out of an incision in the stomach 66, and a bypass section of intestine 72 is attached on one end to the bypass conduit output 56 and on another end to the small intestine 74. The bypass intestine 72 may be attached to the bypass conduit output 56 by a variety of techniques, including by suturing. The primary passage output 52 is left in communication with the inside of the stomach 66. The primary and bypass fluid supply tubes 58, 62 are coupled to their respective fluid connectors inside the stomach 66, passed through the stomach wall, and coupled to respective fluid access points 60, 64 as described previously. In other embodiments, the fluid supply tubes may be permanently coupled to their respective regulators, removing the need for fluid connectors. In still other embodiments, where fluid connectors are used, the fluid supply tubes may be held in place on the fluid connectors and/or on the fluid access points with one or more tube locks as are known to those skilled in the art.

Figure 3A:
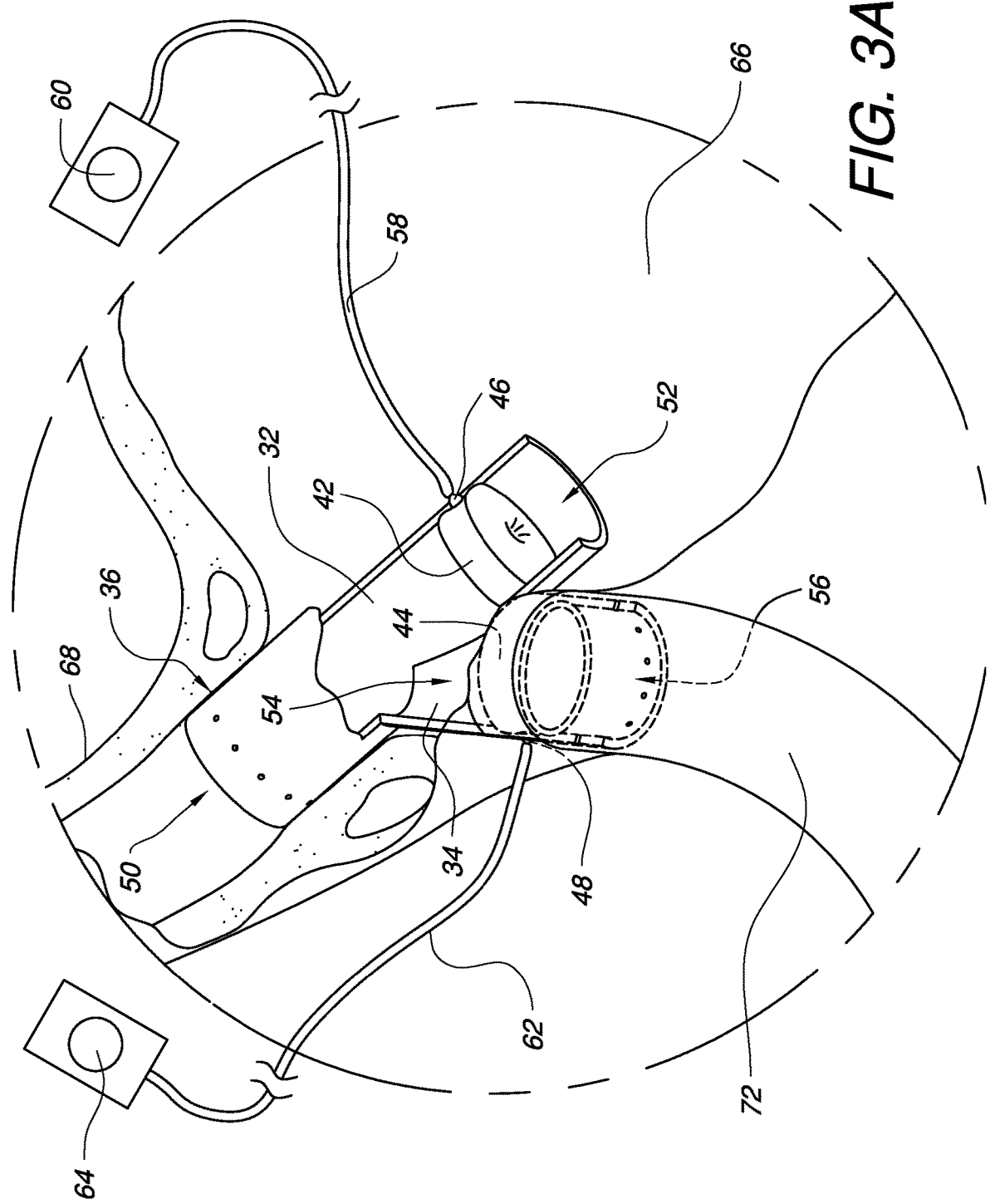
FIG. 3A is an enlarged partially cross-sectioned view of the installed apparatus for gastric bypass from FIG. 3 having a closed primary passage and an open bypass conduit.

FIG. 3A is an enlarged partially cross-sectioned view of the installed gastric bypass apparatus 30 from FIG. 3. The balloon of the primary regulator 42 is completely expanded so that the primary flow profile from the primary passage input 50 to the primary passage output 52 is completely closed. On the other hand, the balloon of the bypass regulator 44 is completely contracted so that the bypass flow profile from the bypass conduit input 54 to the bypass conduit output 56 is completely open. Therefore, with the configuration illustrated in FIG. 3A, food travelling down the esophagus 68 will be blocked from reaching the stomach 66 and instead diverted through the bypass conduit 34 into the bypass intestine 72. Such a configuration can be used to help maximize weight loss.

Figure 3B:
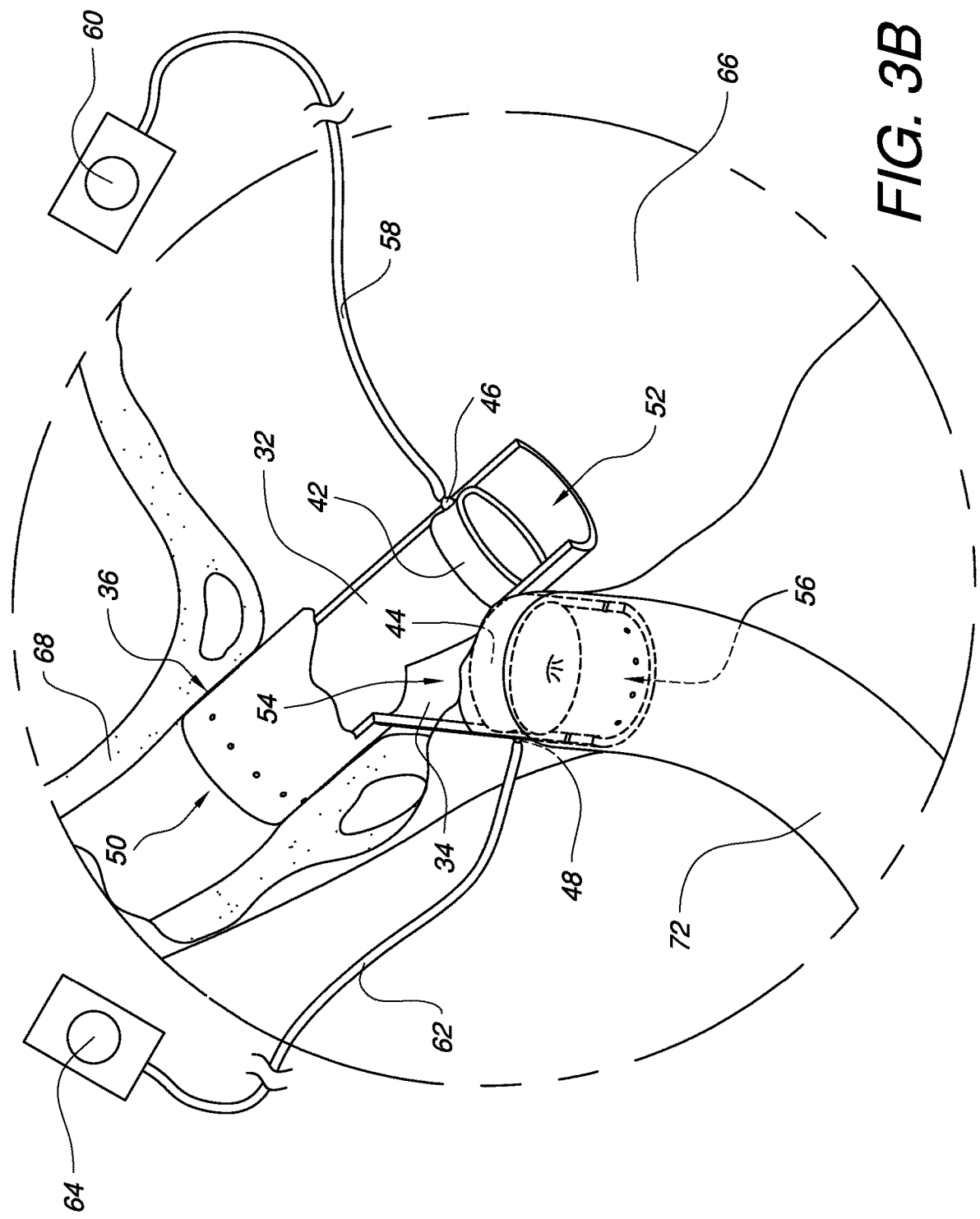
FIG. 3B is an enlarged partially cross-sectioned view of the installed apparatus for gastric bypass from FIG. 3 having an open primary passage and a closed bypass conduit.

The nice thing about such a system is that the gastric bypass is not permanent. In fact, it can easily be adjusted or even reversed by adjusting the primary and bypass regulators 42, 44. FIG. 3B is an enlarged partially cross-sectioned view of the installed gastric bypass apparatus of FIG. 3, this time with fluid added to the bypass regulator 44 and with fluid removed from the primary regulator 42. In the embodiment of FIG. 3B, enough fluid has been removed from the primary regulator 42 that its balloon is completely contracted so that the primary flow profile from the primary passage input 50 to the primary passage output 52 is completely opened. By contrast, enough fluid has been added to the bypass regulator 44 that its balloon is completely expanded so that the bypass flow profile from the bypass conduit input 54 to the bypass conduit output 56 is completely closed. Therefore, with the configuration illustrated in FIG. 3B, food travelling down the esophagus 68 will be blocked from passing into the bypass intestine 72 and, instead, allowed to pass through the primary passage 32 into the stomach 66 for normal digestion. Such a configuration can be used to help augment a patient's nutritional needs when gastric bypass has perhaps been too hard on their body. Such configurations can also be used to temporarily reverse the gastric bypass, for example, in situations such as when the patient has become pregnant. This type of flexibility is enabled by the apparatus and system embodiments disclosed herein as well as their equivalents.

Figure 3C:
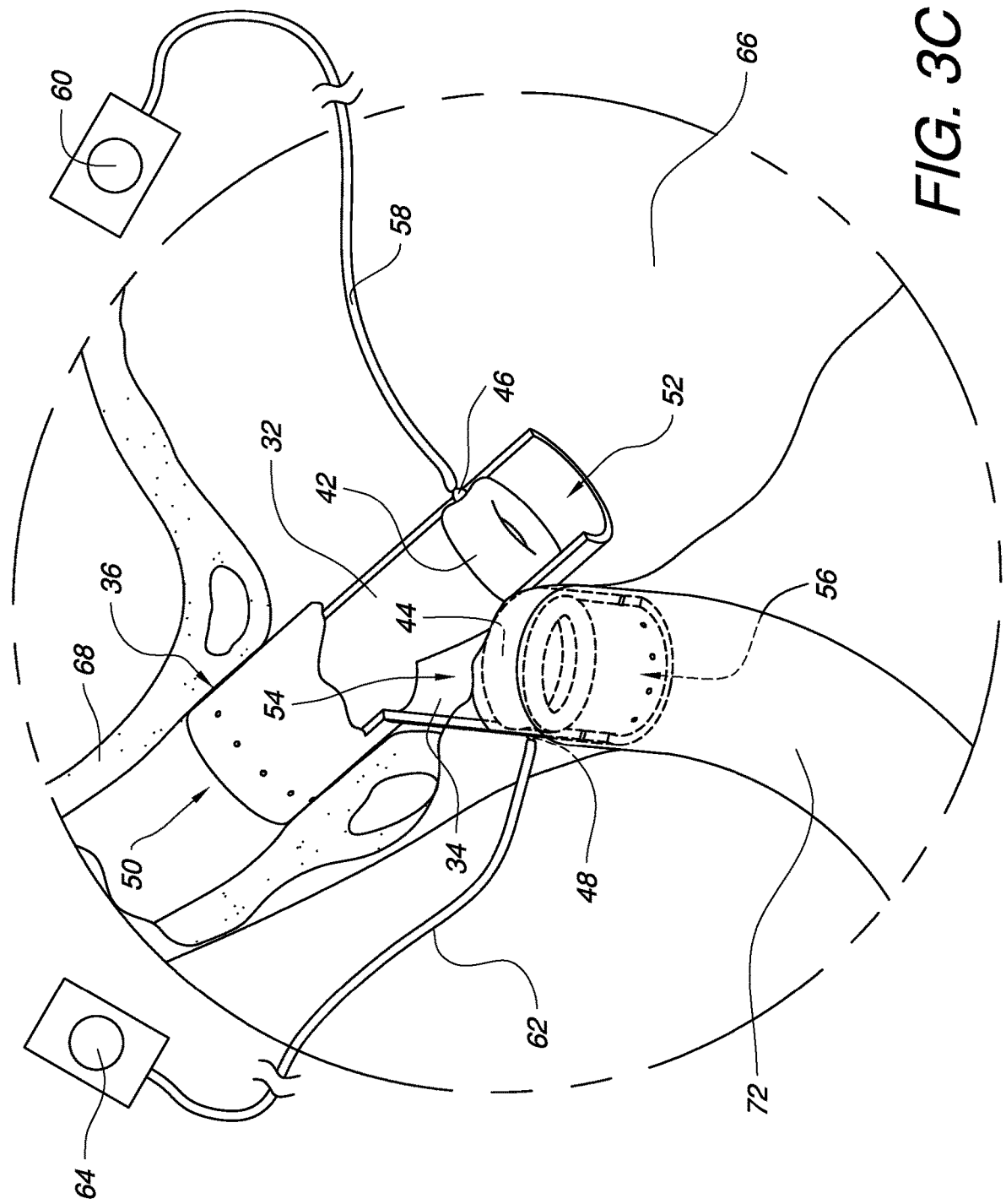
FIG. 3C is an enlarged partially cross-sectioned view of the installed apparatus for gastric bypass from FIG. 3 having a primary passage and a bypass conduit which are both open in differing amounts.

Another benefit which the system flexibility enables is the ability to adjust the primary flow profile and the bypass flow profile such that food has an opportunity to pass through either the primary passage or the bypass passage. For example, FIG. 3C is an enlarged partially cross-sectioned view of the installed gastric bypass apparatus of FIG. 3 having a primary passage 32 and a bypass conduit 34 which are both open different amounts. In the embodiment of FIG. 3C, enough fluid has been added to the primary regulator 42 that its balloon is partially expanded so that the primary flow profile from the primary passage input 50 to the primary passage output 52 is approximately thirty percent of full capacity. The bypass regulator 44 has had fluid removed from the fully expanded state shown in FIG. 3B so that its balloon in FIG. 3C is partially expanded to the point that the bypass flow profile from the bypass conduit input 54 to the bypass conduit output 56 is approximately 70% of full capacity. Therefore, with the configuration illustrated in FIG. 3C, food travelling down the esophagus 68 will partially be able to pass through the primary passage 32 into the stomach, but will mainly pass through the bypass conduit 32 to the bypass intestine 72. Such a configuration can be used to help augment a patient's nutritional needs when gastric bypass has perhaps been too hard on their body, while also keeping a portion of the bypass active. Any combination of primary and bypass flow profiles can be selected by adding or removing a desired amount of fluid to or from each regulator 42, 44.

Figures 1, 4A:
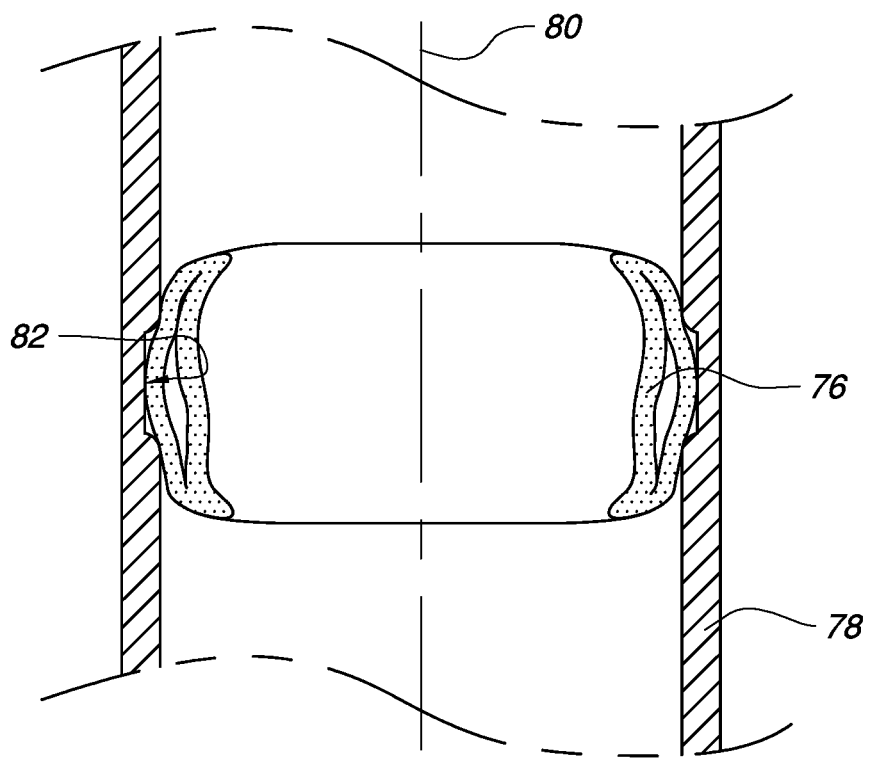
Figures 2, 4A:
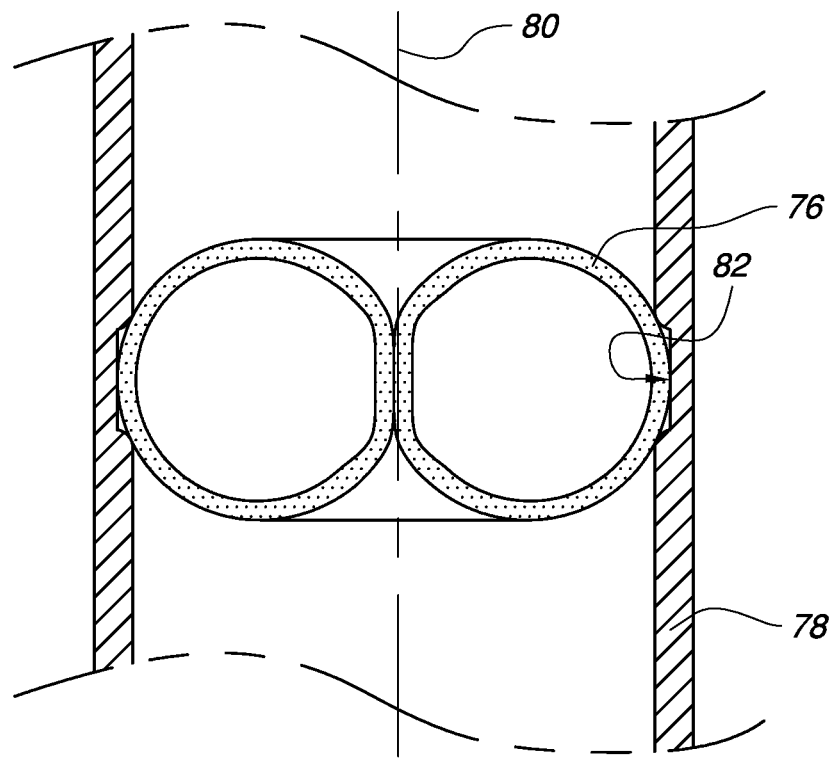
Figures 1, 4B:
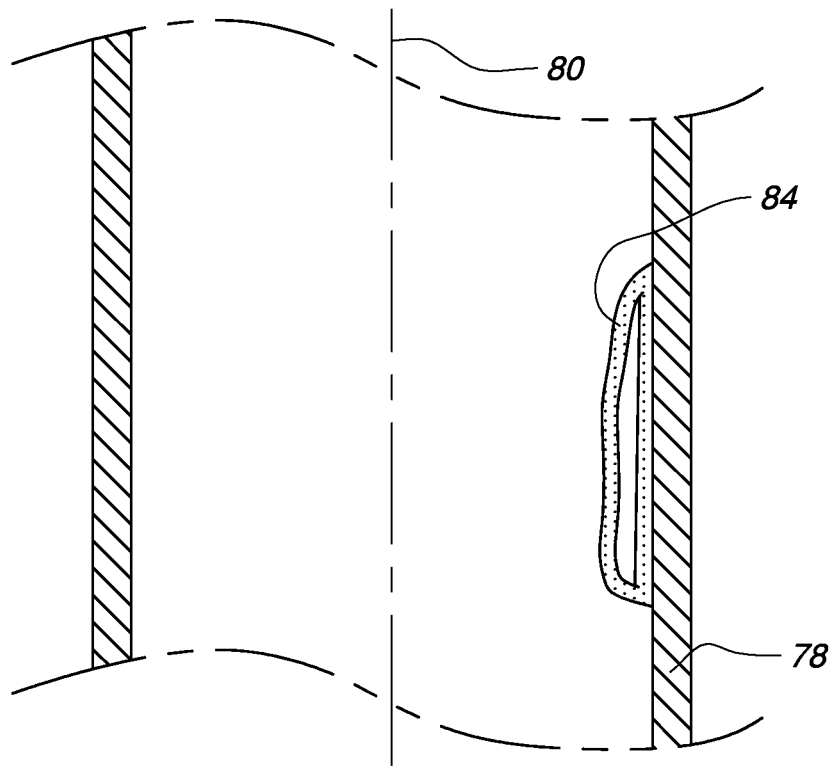
Figures 2, 4B:
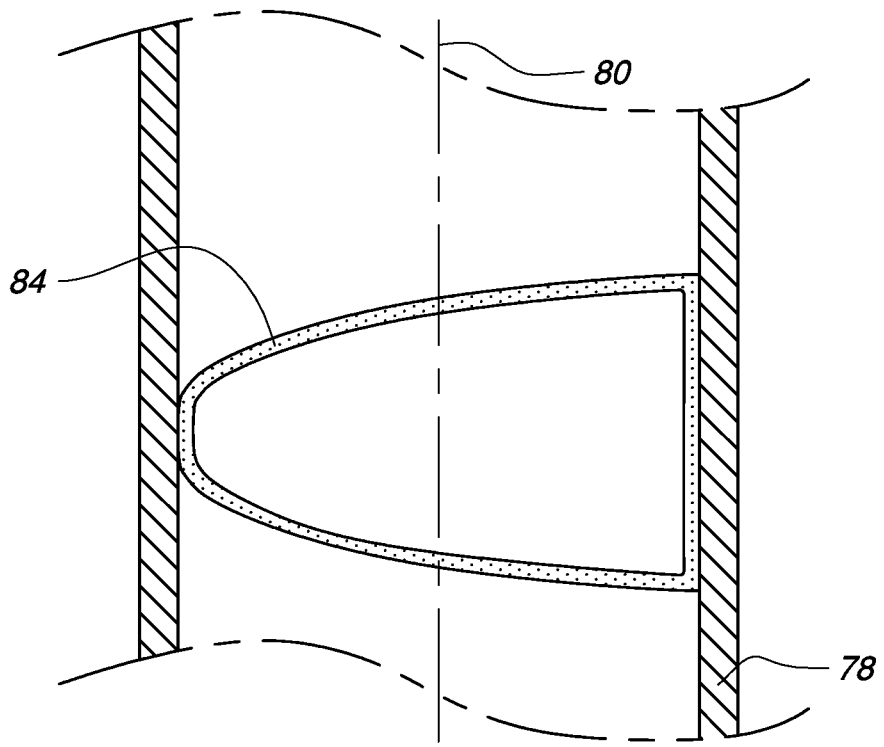

For embodiments where the regulators 42, 44 are inflatable regulators, a wide variety of balloons can be used as part of the regulator. As some non-limiting examples, FIGS. 4A-1 to 5B illustrate various embodiments of inflatable regulators. FIGS. 4A-1 and 4A-2 illustrate cross-sectional views of one embodiment of an inflatable regulator 76 for use in an apparatus for gastric bypass in both open and closed configurations, respectively. The inflatable regulator 76 is coupled within a passage or conduit 78 having a longitudinal axis 80. The passage or conduit 78 may have a groove 82 or other alignment feature to help maintain a position of the inflatable regulator 76. The inflatable regulator 76 may also or alternatively be adhered or otherwise coupled to the inner wall of the passage 78. In the embodiment of FIGS. 4A-1 and 4A-2, the inflatable regulator 76 is a donut-like structure. FIG. 4A-1 shows a cross-section of the donut-like structure deflated with little or no fluid present in the balloon so that the passage 78 is open. FIG. 4A-2 shows a cross-section of the donut-like structure inflated with an appropriate amount of fluid added to the balloon so that the passage 78 is blocked off. In the embodiment of FIGS. 4A-1 and 4A-2, the inflatable regulator 76 is substantially symmetrical around the longitudinal axis 80 of the passage or conduit 78. In other embodiments, however, an inflatable regulator does not need to be substantially symmetrical around the longitudinal axis 80. For example, FIGS. 4B-1 and 4B-2 illustrate cross-sectional views of another embodiment of an inflatable regulator 84 for use in an apparatus for gastric bypass in both open and closed configurations, respectively. FIG. 4B-1 shows a cross-sectional view of the inflatable regulator 84 deflated with little or no fluid present in the balloon so that the passage 78 is open. FIG. 4B-2 shows a cross-section of the inflatable regulator 84 inflated with an appropriate amount of fluid added to the balloon so that the passage 78 is closed. In this embodiment, the inflatable regulator 84 is not substantially symmetrical around the longitudinal axis 80.

Figure 5A:
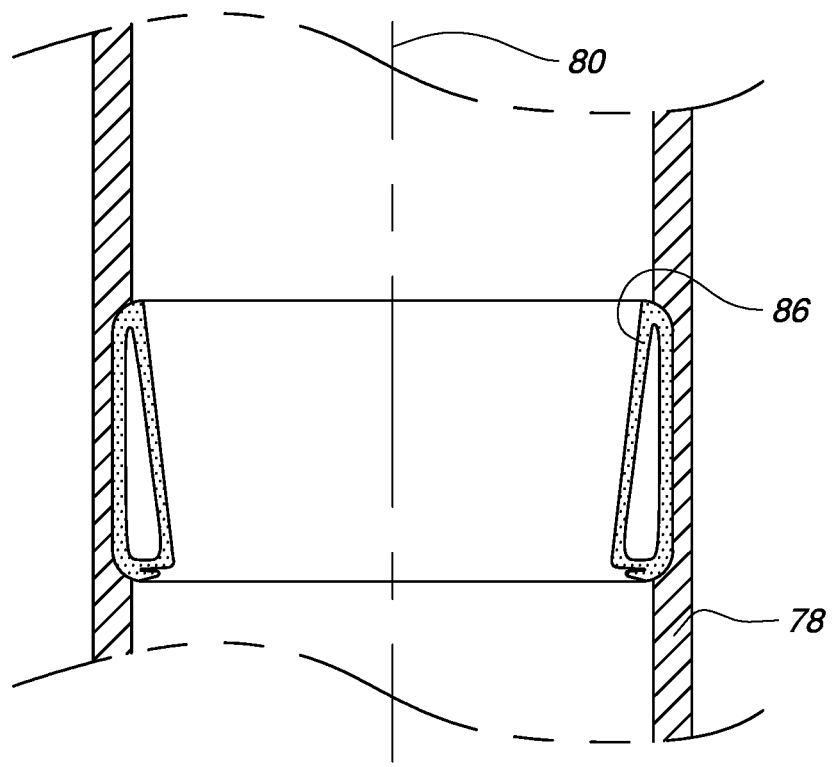
FIGS. 5A and 5B illustrate cross-sectional views of a further embodiment of an inflatable regulator for use in an apparatus for gastric bypass in both open and closed configurations, respectively.
Figure 5B:
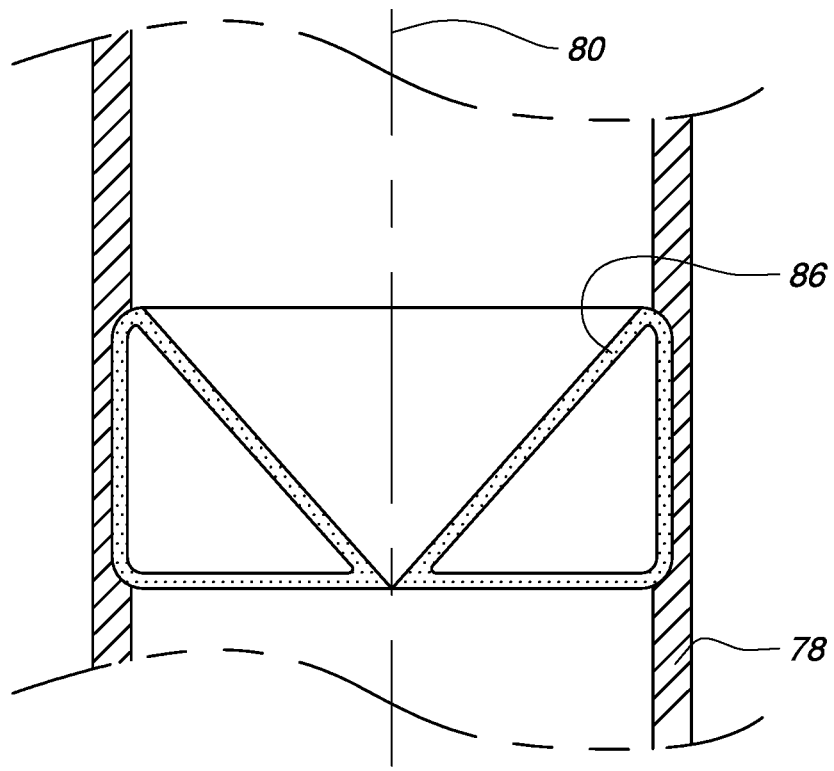

FIGS. 5A and 5B illustrate cross-sectional views of a further embodiment of an inflatable regulator 86 for use in an apparatus for gastric bypass in both open and closed configurations, respectively. FIG. 5A shows a cross-sectional view of the inflatable regulator 86 deflated with little or no fluid present in the balloon so that the passage 78 is open. FIG. 5B shows a cross-section of the inflatable regulator 86 inflated with an appropriate amount of fluid added to the balloon so that the passage 78 is closed. In this embodiment, like the embodiment of FIGS. 4A-1 and 4A-2, the inflatable regulator 86 is substantially symmetrical around the longitudinal axis 80. However, in the embodiment of FIGS. 5A and 5B, unlike the embodiment of FIGS. 4A-1 and 4A-2, the inflatable regulator 86 is not substantially symmetrical about a plane perpendicular to the longitudinal axis 80.

Figure 6:
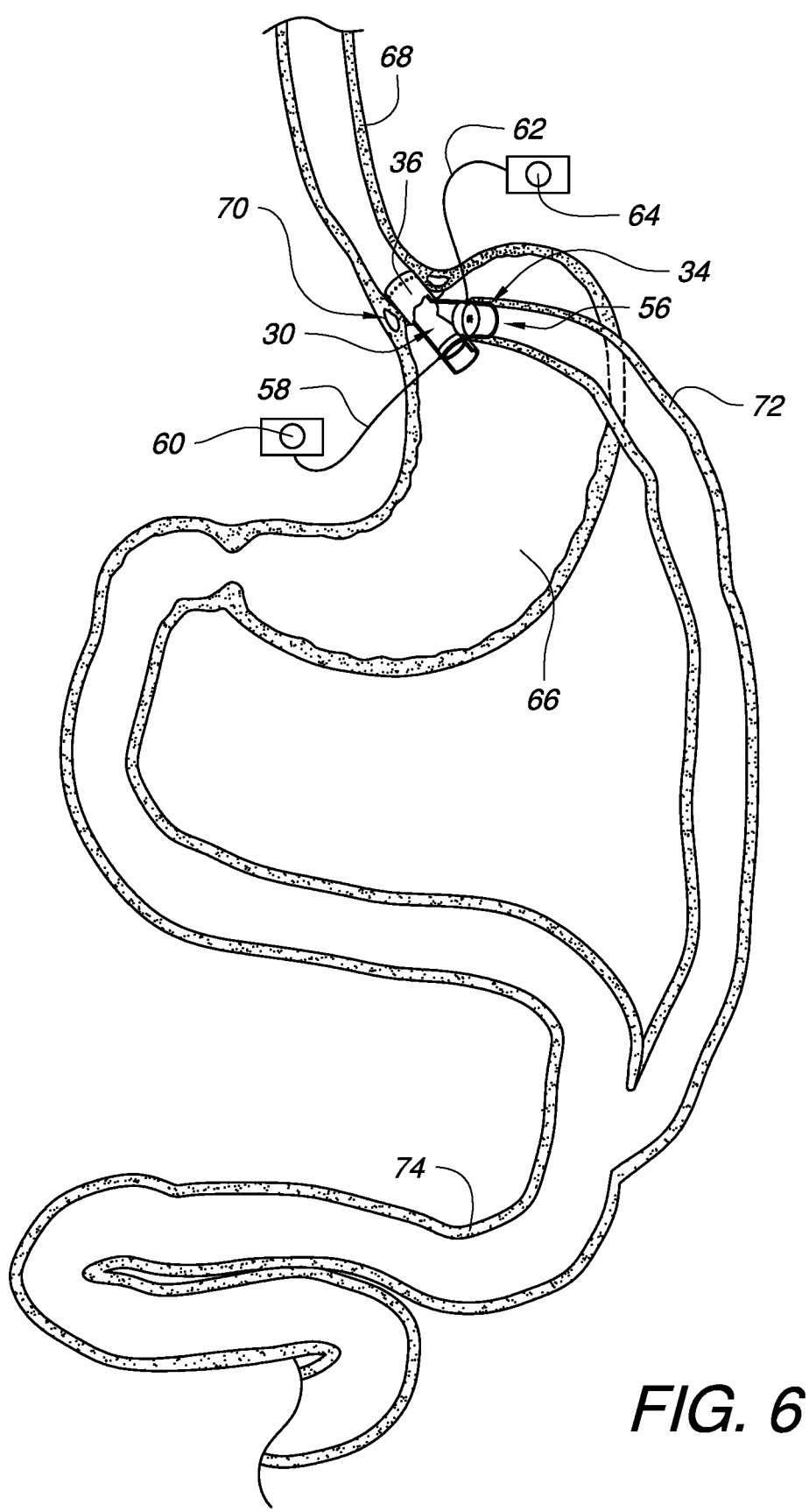
FIG. 6 is a partially cross-sectioned illustration of the apparatus for gastric bypass from FIG. 1 in another possible installed orientation for providing an adjustable gastric bypass to a patient.

As mentioned previously, the gastric bypass apparatus can be rotated so that the bypass conduit 34 faces a desired bypass direction within the stomach 66. In the example of FIG. 3, discussed above, the bypass conduit 34 was oriented slightly towards the patient's right side. As a non-limiting example of another orientation, in the embodiment of FIG. 6, the bypass conduit 34 is oriented towards the patient's left side. The bypass intestine 72 can be routed accordingly, and the gastric bypass apparatus 30 will operate exactly as described previously.

Figure 7:
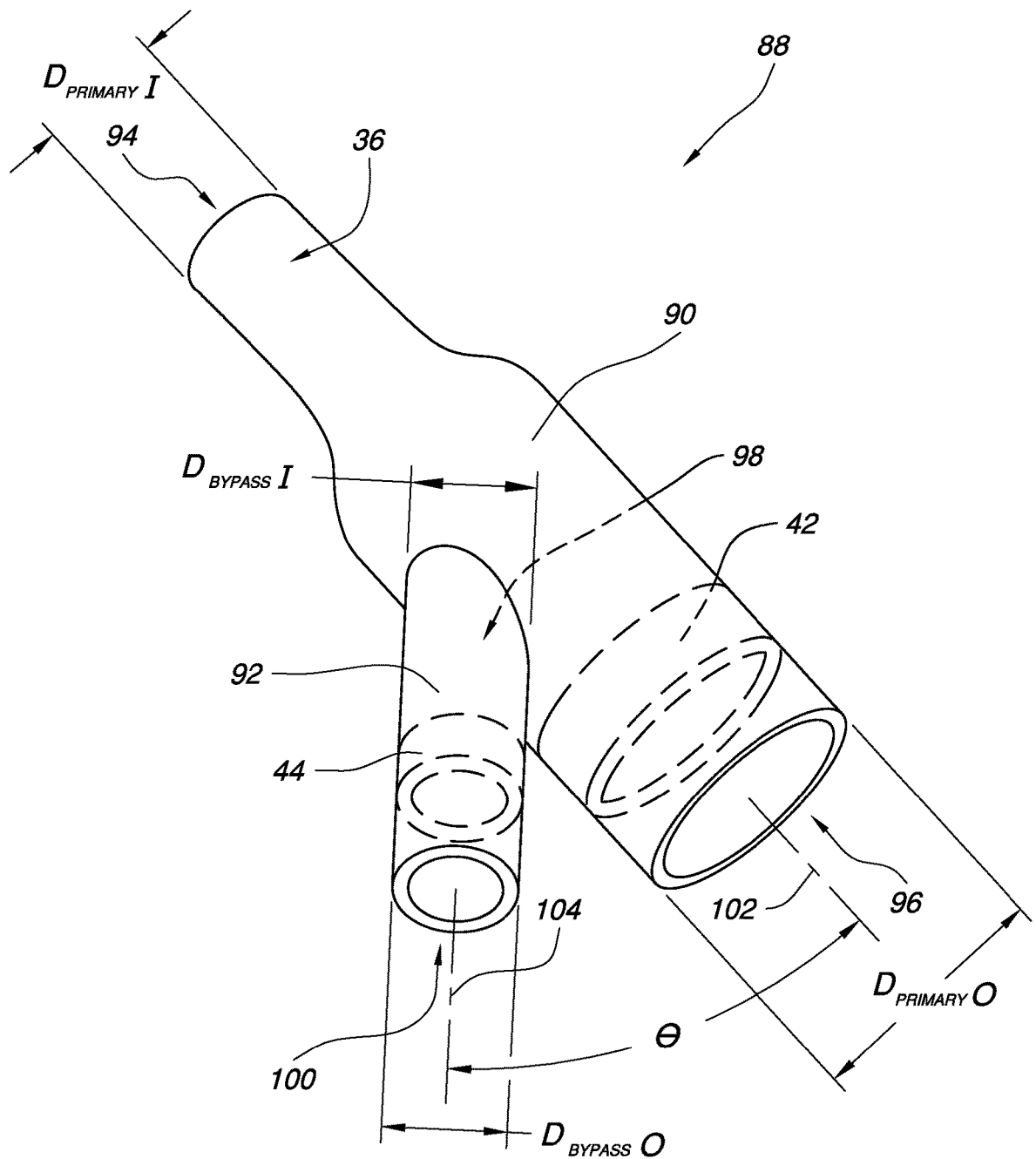
FIG. 7 is a perspective view of another embodiment of an apparatus for gastric bypass.

FIG. 7 is a perspective view of another embodiment of a gastric bypass apparatus 88. The gastric bypass apparatus 88 has a primary passage 90 and a bypass conduit 92. The primary passage 90 and the bypass conduit 92 may be formed of any rigid or flexible biocompatible material, including, but not limited to plastic, silicone, rubber, or even metal. In some embodiments, the material may not be able to be sutured. In such cases, suitable attachment points may be provided to the apparatus 88. The apparatus 88 also has a primary regulator 42 in the primary passage 90 and a bypass regulator 44 in the bypass conduit 92. The features and operation of the primary and bypass regulators 42, 44 have been discussed previously with respect to other embodiments.

The primary passage 90 has an input 94 and an output 96. Likewise, the bypass conduit 92 has an input 98 and an output 100. The primary passage input 94 is interspersed with the bypass conduit input 98, meaning that the two inputs are at least partially in contact or communication with each other. In this embodiment, the primary passage input 94 must be passed through in order to reach the bypass conduit input 98. In other embodiments, the opposite could be the case: that the bypass conduit input must be passed through in order to reach the primary passage input. In still other embodiments, even though the primary passage input and the bypass conduit input are interspersed, there may still be at least a portion of both inputs which can be reached without passing through the other.

The primary passage input 94 has a diameter, $D_{PrimaryI}$. The primary passage output 96 has a diameter, $D_{PrimaryO}$. In this embodiment, the primary passage output diameter $D_{PrimaryO}$ is greater than the primary passage input diameter $D_{PrimaryI}$. In other embodiments, the primary passage input diameter $D_{PrimaryI}$ may be greater than the primary passage output diameter $D_{PrimaryO}$. In still other embodiments, the primary passage input diameter $D_{PrimaryI}$ may be equal to the primary passage output diameter $D_{PrimaryO}$.

Similarly, the bypass conduit input 98 has a diameter, $D_{BypassI}$. The bypass conduit output 100 has a diameter, $D_{BypassO}$. In this embodiment, the bypass conduit output diameter $D_{BypassO}$ is equal to the bypass conduit input diameter $D_{BypassI}$. In other embodiments, the bypass conduit input diameter $D_{BypassI}$ may be greater than or less than the bypass conduit output diameter $D_{BypassO}$. Furthermore, depending on the embodiment, the bypass conduit diameters do not need to be the same as the primary passage diameters, but they can be.

In the gastric bypass apparatus 88 of FIG. 7, both the primary passage 90 and the bypass conduit 92 have a substantially circular cross-section. Other embodiments may have a primary passage and/or a bypass conduit with other types of cross-sections, including, but not limited to oval, hexagonal, octagonal, triangular, square, non-symmetrical, polygon, and non-polygon.

In the gastric bypass apparatus 88 of FIG. 7, the primary passage 90 is substantially straight, following a primary longitudinal axis 102. Similarly, the bypass conduit 92 is substantially straight, following a bypass longitudinal axis 104. In other embodiments, the primary passage and/or the bypass conduit may be curved or follow some other non-linear path.

In this embodiment, the primary longitudinal axis 102 forms an acute angle Θ with the bypass longitudinal axis 104 as measured between the primary passage output 96 and the bypass conduit output 100. In other embodiments, this angle Θ may be a right angle or even obtuse.

Figure 8:
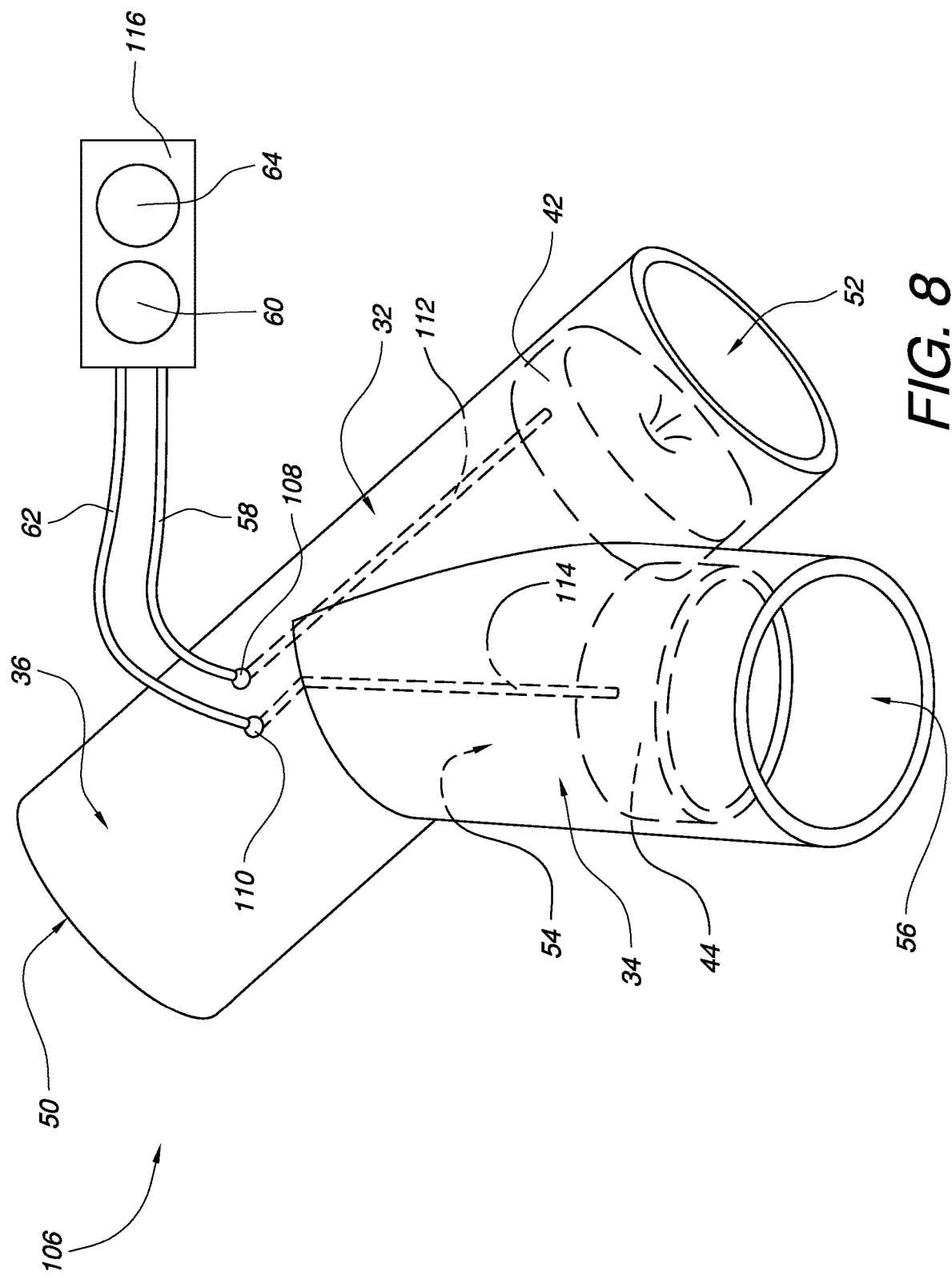
FIG. 8 is a perspective view of a further embodiment of an apparatus for gastric bypass having fluid connectors located remotely from their respective regulators.

In the embodiments illustrated up to this point, the primary and bypass regulators each have had a fluid connector which is in alignment with the regulator. In the embodiment of FIG. 8, however, the embodied gastric bypass apparatus 106 has fluid connectors 108, 110 located remotely from their respective regulators 42, 44. Specifically, the primary fluid connector 108 is coupled to the primary regulator 42 by a channel 112 formed in the wall of the primary passage 32. Similarly, the bypass fluid connector 110 is coupled to the bypass regulator 44 by a channel 114 formed in the wall of the bypass conduit 34 and in the wall of the primary passage 32. Gastric bypass apparatus 106 embodiments having one or more remotely located fluid connectors 108, 110 can have an advantage that the fluid connectors 108, 110 may be located close to each other, thereby making the routing and connection of fluid supply tubes 58, 62 to the connectors 108, 110 from the fluid access points 60, 64 more convenient. This may also be helpful in embodiments where the primary and bypass fluid access points 60, 64 are co-located or part of the same fluid access assembly 116 as schematically illustrated in the embodiment of FIG. 8.

Figure 9:
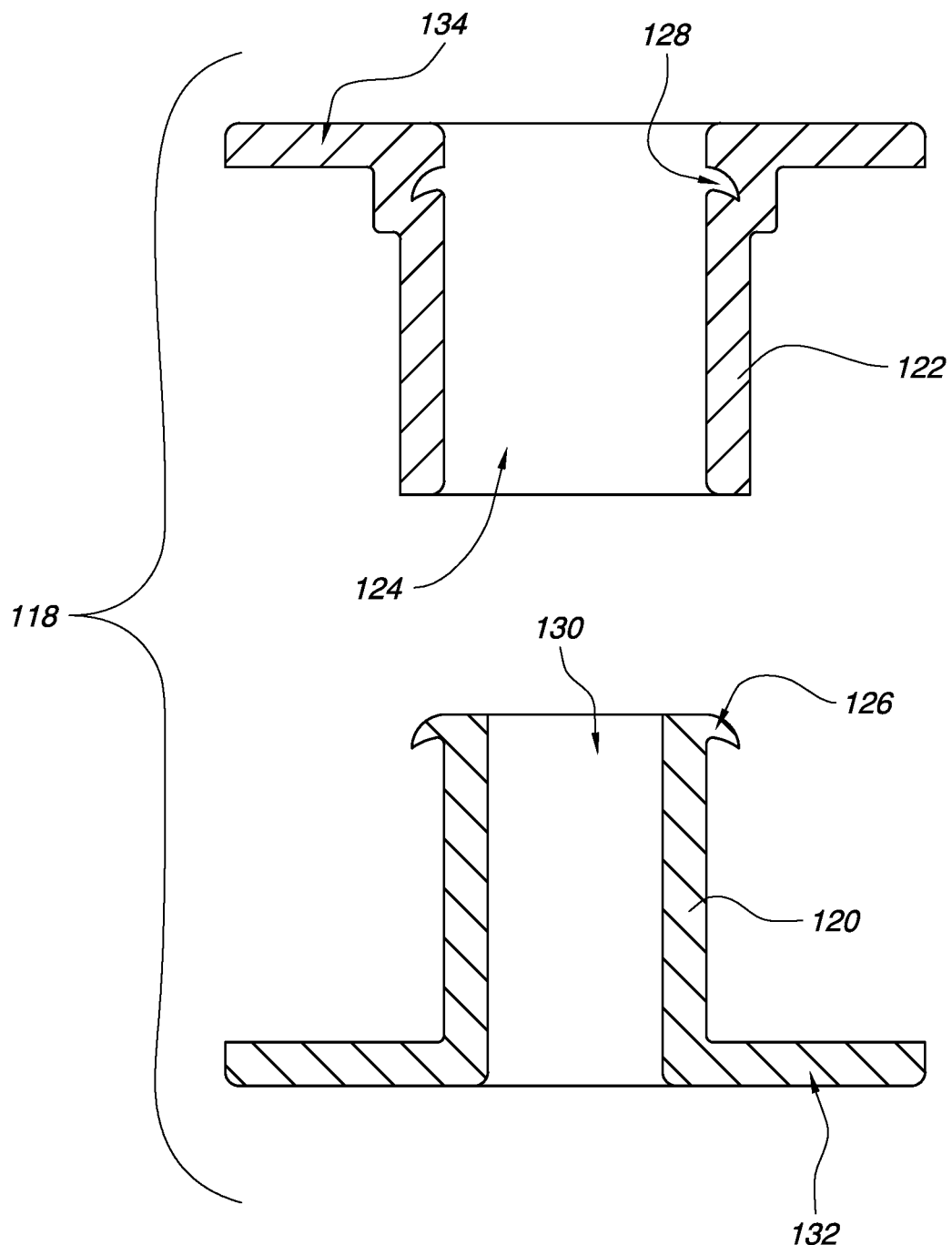
FIG. 9 is a cross-sectional view of one embodiment of a fluid supply gasket for use with a system for gastric bypass.

From a gastric bypass system perspective, the gastric bypass apparatus embodiments discussed above are not the only consideration. In addition to the primary and bypass fluid access points, consideration should also be given to routing of the fluid supply tubes from the gastric bypass apparatus to the fluid access points. In particular, one or more fluid supply tubes will need to be passed through the wall of the stomach. In order to assist a surgeon with the task of passing one or more fluid supply tubes through the wall of the stomach, while preventing stomach contents from leaking out of the stomach, one or more fluid supply gaskets may be used. FIG. 9 is a cross-sectional view of one embodiment of a fluid supply gasket 118 for use with a system for gastric bypass. The fluid supply gasket 118 has a male gasket portion 120 and a female gasket portion 122. The female gasket portion 122 defines a bore 124 which is sized to receive the male gasket portion 120. The male gasket portion 120 may also have at least one interlocking component 126. Similarly, the female gasket portion 122 may have at least one interlocking component 128. When the male gasket portion 120 is inserted into the bore 124 of the female gasket portion 122, the interlocking components 126, 128 will engage and prevent or resist the separation of the male and female gasket portions 120, 122. A variety of interlocking component designs, beyond the embodiment illustrated, could be used and are known to those skilled in the art.

Figure 10:
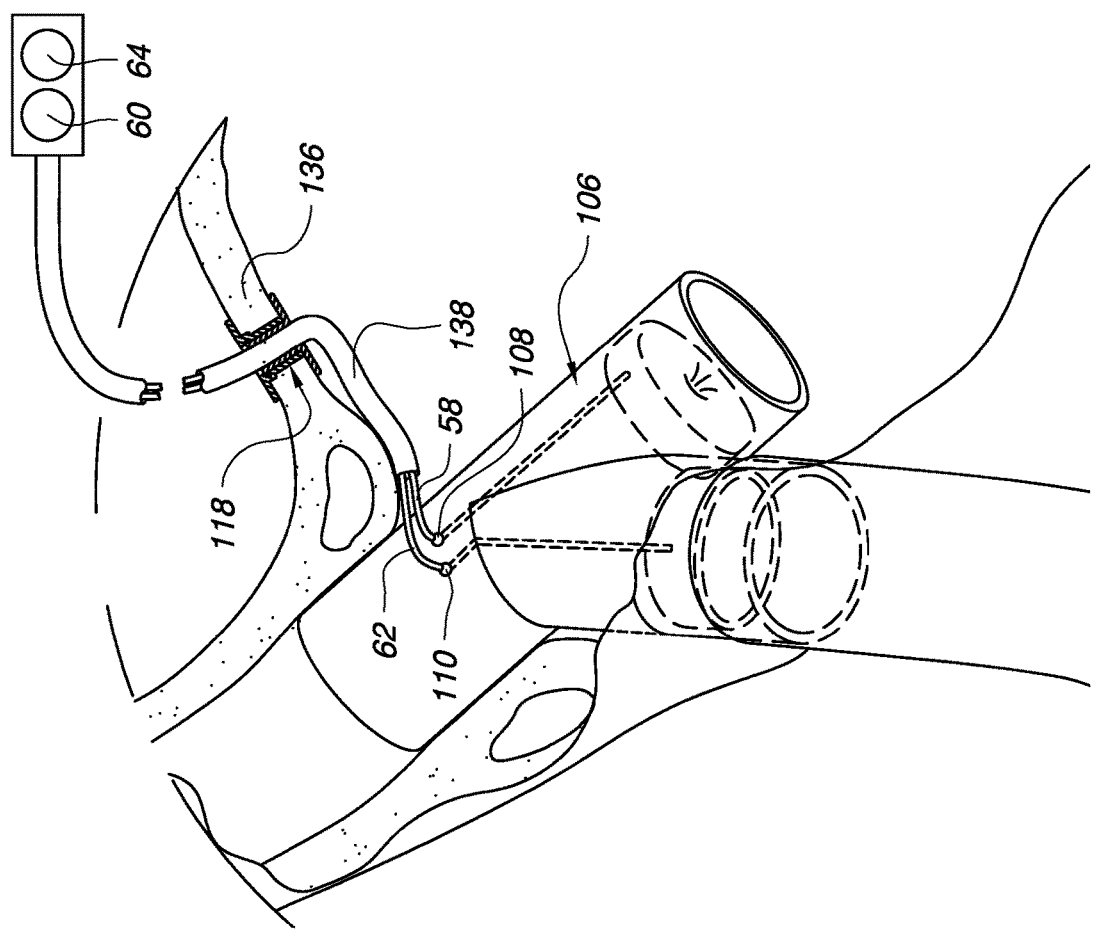
FIG. 10 is a partial cross-sectional view of the apparatus for gastric bypass from FIG. 8 and the fluid supply gasket from FIG. 9 in one possible installed orientation for providing an adjustable gastric bypass to a patient.

The male gasket portion 120 defines a tube channel 130 which is sized to tightly fit one or more fluid supply tubes. The male and female gasket portions 120, 122 also have respective flanges 132, 134. The fluid supply gasket 118 can be locked together from opposite sides of an incision in the stomach wall 136 as illustrated in the partial cross-sectional view of FIG. 10. A larger tube 138, housing the primary fluid supply tube 58 and the bypass fluid supply tube 62, tightly passes through the tube channel of the fluid supply gasket 118. Thus, fluid supply gasket 118 provides a sealed transition for the fluid supply tubes through the stomach wall 136. As before, one end of the fluid supply tubes 58, 62 is connected to their respective fluid connectors 108, 110, while the other end is connected to their respective fluid access points 60, 64. The features of the gastric bypass apparatus 106 shown in FIG. 10 have been discussed previously.

As described previously, some embodiments of a gastric bypass apparatus may be made from a material which can be sutured, either because a needle can be used to penetrate the apparatus or because suturing holes have been provided in the apparatus. Other embodiments may use other techniques in addition to suturing. For example, FIG. 11 is a perspective view of another embodiment of a gastric bypass apparatus 140. The gastric bypass apparatus 140 has a primary passage 32, a bypass conduit 34, and primary and bypass regulators (not visible in this view), the features of which have been discussed above. The gastric bypass apparatus 140, however, has multiple piercing latches 142 on the esophageal interface 36 and on the bypass conduit 34 to assist with installation of the apparatus 140. The embodied latches 142 have a sharp tip for penetrating tissue. The sharp tip widens as it approaches the apparatus 140 and then narrows into a shaft protruding from the apparatus 140. Tissue pressed over the sharp tip can expand back around the narrow shaft after passing by the wider portion. The wider portion may help to resist movement of the pierced tissue away from the apparatus. In some embodiments, a band, such as the band 144 shown in the top and side views of FIGS. 12A and 12B, respectively, may be used to help hold pierced tissue in place in the vicinity of and between the piercing latches 142. Such a situation is shown in FIG. 13. FIG. 13 is a cross-sectional view of a portion of the bypass conduit 34 from the apparatus of FIG. 11. A bypass intestine 72 has been placed over the bypass conduit output 56. The bypass intestine 72 has been pierced by the piercing latches 142. A band 144 has been wrapped around the bypass conduit 34 and over the bypass intestine 72. The band 144 has also been pierced by the piercing latches 142. As shown in the embodiment of FIGS. 12A and 12B, the band 144 may be provided with holes 146 to make it easier for the piercing latches 142 to pierce the band 144. In other embodiments, the band 144 may not have any holes 146. The band 144 may have a thickness T which allows the band to extend higher than the tip of the piercing latches 142 as shown in FIG. 13. In such embodiments, this can help to protect other internal tissue from being pierced by the piercing latches 142 after the band 144 has been installed. In some embodiments, the band 144 may also have one or more tissue-side recesses 148 to enable tissue held by the band 144 to still maintain blood flow in order to prevent ischemia. The band 144, in conjunction with the piercing latches 142, help to hold the bypass intestine 72 against the bypass conduit 34 and to maintain a good seal so that gastrointestinal contents stay within the gastrointestinal tract.

Since the bypass conduit 34 must pass through an opening created in the stomach wall, surgeons will need to ensure that this opening is also sealed. As one example of how this might be done, in FIG. 13, sutures 150 may be placed through a portion of the bypass intestine 72 and the stomach wall 152. The sutures 150 can be secured by a variety of techniques known to those skilled in the art, including, but not limited to securing with a crimpable metal fastener such as the Ti-KNOT® fastener 154 from LSI Solutions, Inc. of Victor, N.Y.

Figure 14:
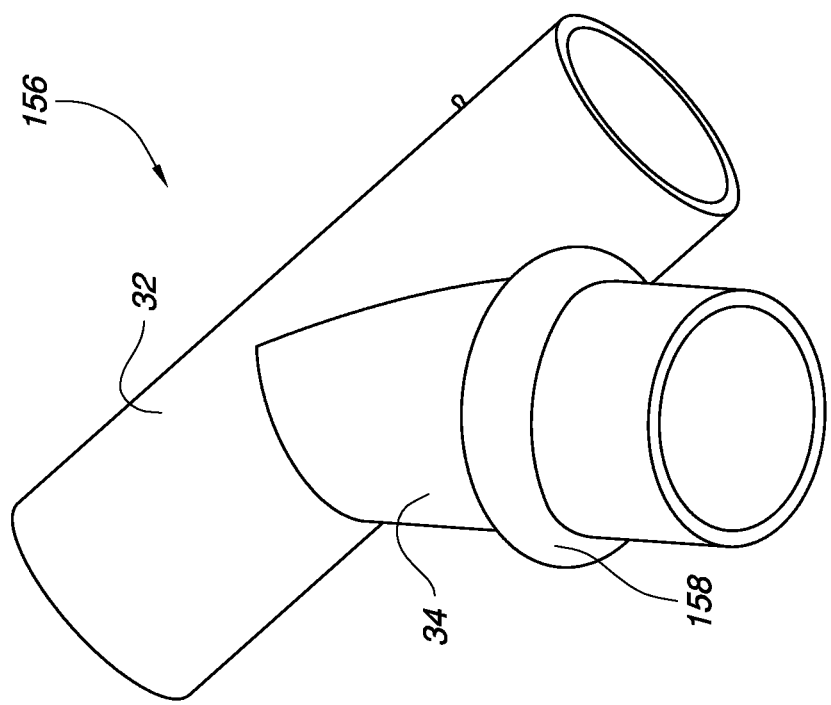
FIG. 14 is a perspective view of a further embodiment of an apparatus for gastric bypass having a stomach connection flange to assist with installation of the apparatus.

In some instances, the bypass intestine 72 may not be strong enough or large enough to suture to the stomach wall in such a fashion as to seal the opening made for the bypass conduit 34. In such instances, embodiments of a gastric bypass apparatus can include an additional feature to assist with the closure of the stomach around the incision for the bypass conduit 34. For example, FIG. 14 is a perspective view of another embodiment of a gastric bypass apparatus 156. The gastric bypass apparatus 156 has a primary passage 32, a bypass conduit 34, and primary and bypass regulators (not visible in this view), the features of which have been discussed above. The gastric bypass apparatus 156 also has a stomach connection flange 158 around the bypass conduit 34. The stomach connection flange 158 is configured to fit against the stomach wall 160 as illustrated in the cross-sectional view of FIG. 15. Sutures 162 may be placed through the stomach wall 160 and the stomach connection flange 158 and secured by a variety of techniques, including with a crimpable fastener 154 as discussed above. Although the stomach connection flange 158 is shown as being positioned against the stomach wall 160 on the inside of the stomach in the embodiment of FIG. 15, in other embodiments, the stomach connection flange 158 could be sutured on the outside of the stomach. Depending on the embodiment, the stomach connection flange 158 can be a continuous part of the bypass conduit 34 or an additional component coupled to the bypass conduit 34.

Figure 15:
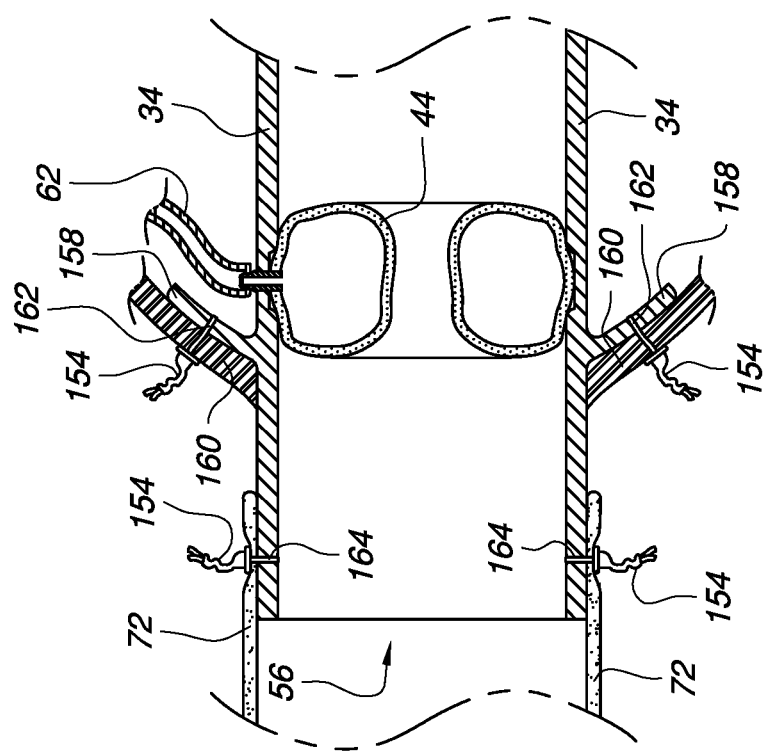
FIG. 15 is a cross-sectional view of a portion of the bypass conduit from the apparatus of FIG. 14 showing one possible attachment embodiment for tissues outside the stomach and for sealing to tissues of the stomach.

In the embodiment of FIG. 15, the bypass conduit 34 is made from a material which is able to be sutured, so the bypass intestine 72 is sutured to the bypass conduit output 72 by sutures 164. As with the sutures discussed above, the sutures 164 may be secured by a variety of techniques, including with a crimpable fastener 154.

Figure 16:
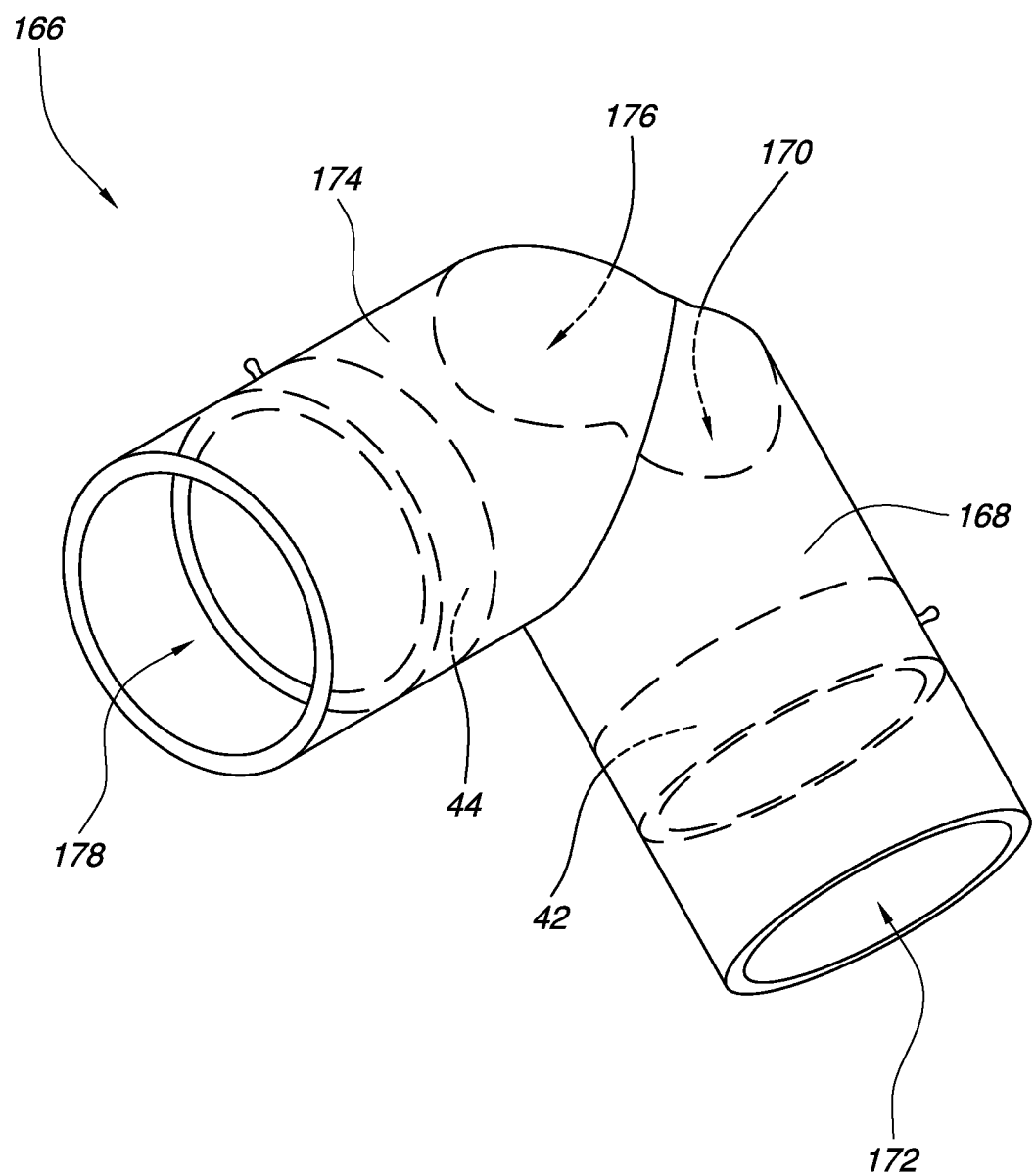
FIG. 16 is a perspective view of another embodiment of an apparatus for gastric bypass.

FIG. 16 is a perspective view of another embodiment of an apparatus for gastric bypass 166. The gastric bypass apparatus 166 has a primary passage 168 having an input 170 and an output 172. The gastric bypass apparatus 166 also has a bypass conduit 174 coupled to the primary passage 168. The bypass conduit 174 has an input 176 and an output 178. As with previous embodiments, the bypass conduit input 176 is interspersed with the primary passage input 170. The gastric bypass apparatus also has a primary regulator 42 coupled to the primary passage 168 and adjustable to control a primary flow profile from the primary passage input 170 to the primary passage output 172 in a manner as discussed with previous embodiments. Similarly, the gastric bypass apparatus also has a bypass regulator 44 coupled to the bypass conduit 174 and adjustable to control a bypass flow profile from the bypass conduit input 176 to the bypass conduit output 178 in a manner as discussed with previous embodiments. In this embodiment, the apparatus 166 does not have an esophageal interface. Furthermore, the apparatus is configured such that at least some food received from an esophagus can pass into the bypass conduit input 176 without having to pass through the primary passage input 170.

Figure 17:
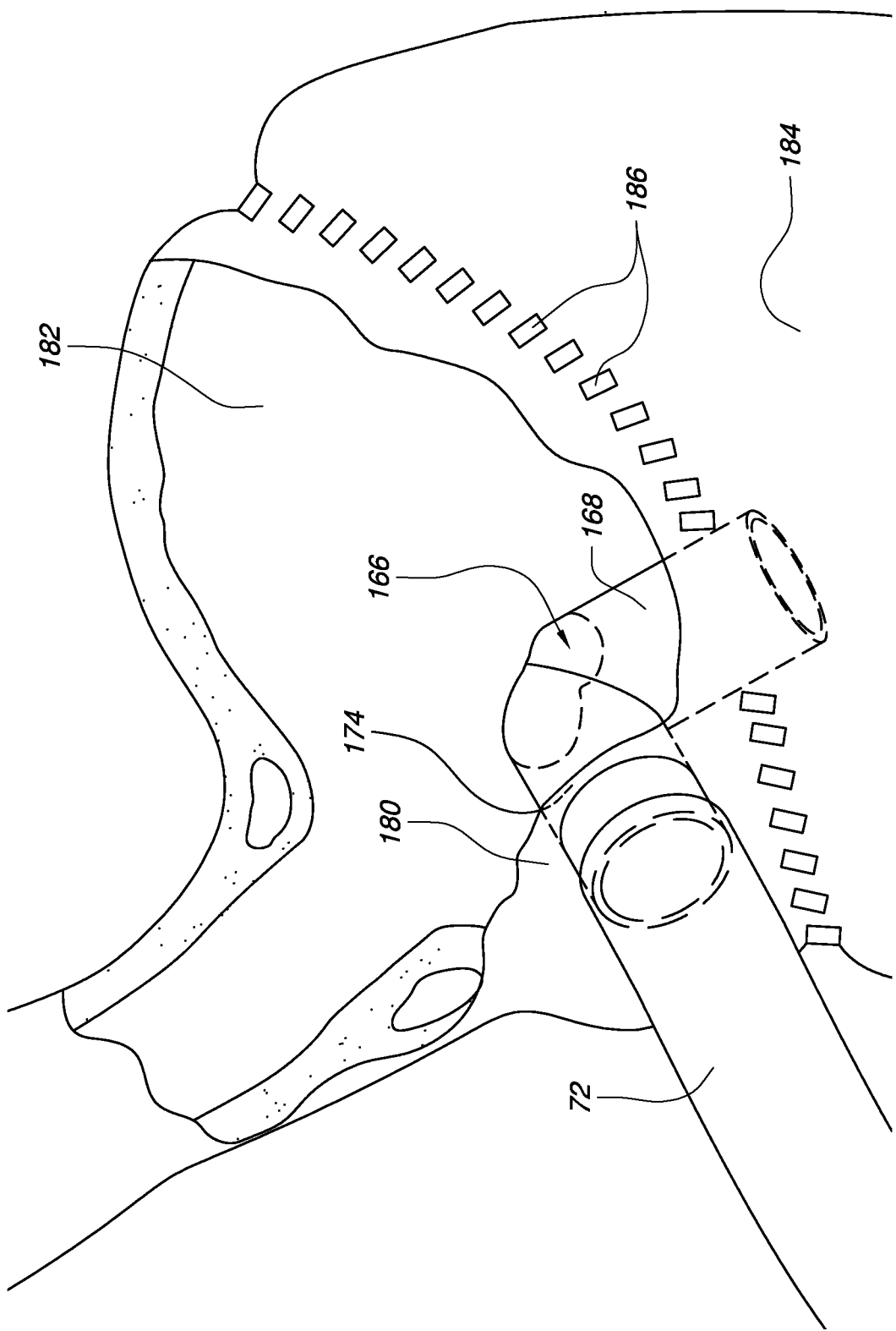
FIG. 17 is a partially cross-sectioned illustration of the apparatus for gastric bypass from FIG. 16 in one possible installed orientation for providing an adjustable gastric bypass to a patient.

Since the gastric bypass apparatus 166 does not have an esophageal interface, the apparatus can still be used with a stomach bypass procedure by coupling the bypass conduit 174 through the stomach wall 180 in a manner as described previously, or in a similar fashion, as shown in the partially cross-sectioned illustration of FIG. 17. The primary passage 168 can be secured within the stomach as a passage between an upper stomach pouch 182 and a lower stomach pouch 184 formed by a line of staples 186 or other similar stomach splitting technique known to those skilled in the art. The primary and bypass regulators, fluid supply tubes, and fluid access points (not shown in this view for simplicity) all can operate similarly to the embodiments described previously so that the patent can conveniently adjust between a bypass with a small stomach pouch 182 and no bypass with food passing through both the upper and lower stomach pouches 182, 184.

Various advantages of an apparatus and system for adjustable gastric bypass have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. An apparatus for gastric bypass, comprising:
a primary passage having an input and an output, wherein the primary passage input has a different size than the primary passage output;
a bypass conduit, coupled to the primary passage, having an input and an output, wherein the passage input is interspersed with the conduit input;
a primary regulator coupled to the primary passage and adjustable to control a primary flow profile from the input to the output of the primary passage; and a bypass regulator coupled to the bypass conduit and adjustable to control a bypass flow profile from the input to the output of the bypass conduit.

2. The apparatus of claim 1, configured such that food received from an esophagus must pass through at least a portion of the primary passage input in order to reach the bypass conduit input.

3. The apparatus of claim 1, wherein:
the primary passage comprises a substantially circular cross-section; and
the bypass conduit comprises a substantially circular cross-section.

4. The apparatus of claim 1, wherein the primary passage is substantially straight.

5. The apparatus of claim 1, wherein the bypass conduit is substantially straight.

6. The apparatus of claim 1, wherein:
the primary regulator comprises an inflatable device; and/or
the bypass regulator comprises an inflatable device.

7. The apparatus of claim 6, wherein the inflatable device of the bypass regulator comprises a donut-like shape.

8. The apparatus of claim 1, further comprising:
a primary fluid connector coupled to the primary regulator; and
a bypass fluid connector coupled to the bypass regulator.

9. The apparatus of claim 1, further comprising:
an esophageal interface.

10. The apparatus of claim 9, wherein the esophageal interface comprises a material which can be sutured.

11. The apparatus of claim 9, wherein the esophageal interface comprises one or more suture holes.

12. An apparatus for gastric bypass, comprising:
a primary passage having an input and an output;
a bypass conduit, coupled to the primary passage, having an input and an output, wherein the passage input is interspersed with the conduit input, and wherein the bypass conduit input has a different size than the bypass conduit output;
a primary regulator coupled to the primary passage and adjustable to control a primary flow profile from the input to the output of the primary passage; and
a bypass regulator coupled to the bypass conduit and adjustable to control a bypass flow profile from the input to the output of the bypass conduit.

13. The apparatus of claim 12, configured such that food received from an esophagus must pass through at least a portion of the primary passage input in order to reach the bypass conduit input.

14. The apparatus of claim 12, wherein:
the primary passage comprises a substantially circular cross-section; and
the bypass conduit comprises a substantially circular cross-section.

15. The apparatus of claim 12, wherein the primary passage is substantially straight.

16. The apparatus of claim 12, wherein the bypass conduit is substantially straight.

17. The apparatus of claim 12, wherein:
the primary regulator comprises an inflatable device; and/or
the bypass regulator comprises an inflatable device.

18. The apparatus of claim 12, further comprising:
a primary fluid connector coupled to the primary regulator; and
a bypass fluid connector coupled to the bypass regulator.

19. The apparatus of claim 12, further comprising:
an esophageal interface.

20. The apparatus of claim 19, wherein the esophageal interface comprises a material which can be sutured.

21. The apparatus of claim 19, wherein the esophageal interface comprises one or more suture holes.

22. An apparatus for gastric bypass, comprising:
a primary passage having an input and an output;
a bypass conduit, coupled to the primary passage, having an input and an output, wherein the passage input is interspersed with the conduit input, and wherein the primary passage has a different size from the bypass conduit;
a primary regulator coupled to the primary passage and adjustable to control a primary flow profile from the input to the output of the primary passage; and
a bypass regulator coupled to the bypass conduit and adjustable to control a bypass flow profile from the input to the output of the bypass conduit.

23. The apparatus of claim 22, configured such that food received from an esophagus must pass through at least a portion of the primary passage input in order to reach the bypass conduit input.

24. The apparatus of claim 22, wherein:
the primary passage comprises a substantially circular cross-section; and
the bypass conduit comprises a substantially circular cross-section.

25. The apparatus of claim 22, wherein the primary passage is substantially straight.

26. The apparatus of claim 22, wherein the bypass conduit is substantially straight.

27. The apparatus of claim 22, wherein:
the primary regulator comprises an inflatable device; and/or
the bypass regulator comprises an inflatable device.

28. The apparatus of claim 27, wherein the inflatable device of the bypass regulator comprises a donut-like shape.

29. The apparatus of claim 22, further comprising:
a primary fluid connector coupled to the primary regulator; and
a bypass fluid connector coupled to the bypass regulator.

30. The apparatus of claim 22, further comprising:
an esophageal interface.

31. The apparatus of claim 30, wherein the esophageal interface comprises a material which can be sutured.

32. The apparatus of claim 30, wherein the esophageal interface comprises one or more suture holes.

* * * * *